US011751554B2

(12) United States Patent
Chang et al.

(10) Patent No.: US 11,751,554 B2
(45) Date of Patent: Sep. 12, 2023

(54) ADHESIVE-TYPE INSECT TRAP HAVING A MAIN BODY FOR GUIDING AND STOPPING MOVEMENT OF AN ADHESIVE SHEET

(71) Applicant: SEOUL VIOSYS CO., LTD., Gyeonggi-do (KR)

(72) Inventors: Sang Hyun Chang, Gyeonggi-do (KR); Hoon Sik Eom, Gyeonggi-do (KR); Si Ho Yu, Gyeonggi-do (KR); Gwang Ryong Lee, Gyeonggi-do (KR); Chung Hoon Lee, Gyeonggi-do (KR); Sung Il Park, Gyeonggi-do (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 547 days.

(21) Appl. No.: 16/477,131

(22) PCT Filed: Jan. 5, 2018

(86) PCT No.: PCT/KR2018/000268
§ 371 (c)(1),
(2) Date: Jul. 10, 2019

(87) PCT Pub. No.: WO2018/131840
PCT Pub. Date: Jul. 19, 2018

(65) Prior Publication Data
US 2019/0357516 A1 Nov. 28, 2019

(30) Foreign Application Priority Data

Jan. 10, 2017 (KR) .......................... 10-2017-0003381
Jun. 8, 2017 (KR) .......................... 10-2017-0071843
(Continued)

(51) Int. Cl.
*A01M 1/14* (2006.01)
*A01M 1/02* (2006.01)
(Continued)

(52) U.S. Cl.
CPC ................ *A01M 1/14* (2013.01); *A01M 1/02* (2013.01); *A01M 1/106* (2013.01); *A01M 1/145* (2013.01);
(Continued)

(58) Field of Classification Search
CPC .. A01M 1/14; A01M 1/145; A01M 2200/012; A01M 1/106; A01M 1/165; A01M 1/10; A01M 1/103
See application file for complete search history.

(56) References Cited

U.S. PATENT DOCUMENTS 5,651,211 A * 7/1997 Regan .................... A01M 1/145
43/116
5,934,019 A * 8/1999 Rotharmel .............. E05F 15/43
49/28
(Continued)

FOREIGN PATENT DOCUMENTS

CN 203087336 7/2013
CN 203897100 10/2014
(Continued)

OTHER PUBLICATIONS

Supplementary European Search Report issued in European Application No. 18738568.7, dated Sep. 11, 2020.
(Continued)

*Primary Examiner* — Peter M Poon
*Assistant Examiner* — Carly W. Lynch
(74) *Attorney, Agent, or Firm* — Perkins Coie LLP

(57) ABSTRACT

An adhesive-type insect trap includes a main body having an adhesive sheet insertion hole; a light source mounting unit disposed on the main body; a cover which is detachably mounted on the main body and has a through-hole in at least a part thereof; an adhesive sheet including a sticky substance and a sheet. The main body includes a guide unit by which
(Continued)

the adhesive sheet is guided, and an adhesive sheet support unit for supporting the adhesive sheet.

15 Claims, 36 Drawing Sheets

(30) Foreign Application Priority Data

Jul. 14, 2017 (KR) .................. 10-2017-0089813
Aug. 1, 2017 (KR) .................. 10-2017-0097770

(51) Int. Cl.
*A01M 1/16* (2006.01)
*A01M 1/10* (2006.01)
*G01J 1/44* (2006.01)
*G01V 8/12* (2006.01)

(52) U.S. Cl.
CPC .............. *A01M 1/165* (2013.01); *G01J 1/44* (2013.01); *G01V 8/12* (2013.01)

(56) References Cited

U.S. PATENT DOCUMENTS

| | | | | |
|---|---|---|---|---|
| 6,389,738 | B1 * | 5/2002 | Denny | A01M 1/2011 43/58 |
| 2002/0032980 | A1 | 3/2002 | Nelson | |
| 2003/0079398 | A1 * | 5/2003 | Holmes | A01M 1/145 43/113 |
| 2003/0089024 | A1 * | 5/2003 | Nelson | A01M 1/145 43/113 |
| 2005/0274058 | A1 * | 12/2005 | Miller | A01M 1/145 43/114 |
| 2006/0053683 | A1 * | 3/2006 | Lau | A01M 1/223 43/112 |
| 2007/0124987 | A1 * | 6/2007 | Brown | A01M 1/023 43/113 |
| 2012/0005947 | A1 * | 1/2012 | Studer | A01M 1/145 43/58 |
| 2014/0259878 | A1 * | 9/2014 | Gilbert, II | A01M 1/145 43/113 |

FOREIGN PATENT DOCUMENTS

| | | | | |
|---|---|---|---|---|
| CN | 203897100 U | * | 10/2014 | ............ A01M 1/04 |
| GB | 2459717 | | 11/2009 | |
| JP | 2009-043635 | | 2/2009 | |
| JP | 4256441 | | 4/2009 | |
| JP | 2009183164 | | 8/2009 | |
| JP | 5216054 | | 6/2013 | |
| JP | 2016509843 | | 4/2016 | |
| KR | 100538043 B1 | * | 12/2005 | ............ A01M 1/145 |
| KR | 1020080107918 | | 12/2008 | |
| KR | 2020080006034 | | 12/2008 | |
| KR | 100895486 | | 5/2009 | |
| KR | 100895489 | | 5/2009 | |
| KR | 10-2009-0064070 | | 6/2009 | |
| KR | 100968199 | | 7/2010 | |
| KR | 1020100078422 | | 7/2010 | |
| KR | 1020110128559 A | | 11/2011 | |
| KR | 1020120073476 | | 7/2012 | |
| KR | 1020120139354 | | 12/2012 | |
| KR | 101266861 | | 5/2013 | |
| KR | 101573714 | | 12/2015 | |
| KR | 2020160001863 | | 6/2016 | |
| KR | 10-2016-0098791 | | 8/2016 | |
| KR | 20160098791 A | * | 8/2016 | ............ A01M 1/24 |
| KR | 101681743 | | 12/2016 | |
| WO | 2016207430 | | 12/2016 | |

OTHER PUBLICATIONS

Supplementary European Search Report issued in European Application No. 18738947.3, dated Sep. 11, 2020.
Office Action issued in corresponding Indian Application No. 201937032046, dated Jan. 18, 2021.
International Search Report for International Application No. PCT/KR2018/000268, dated Apr. 24, 2018.
International Search Report for International Application No. PCT/KR2018/000344, dated Apr. 25, 2018.
International Search Report for International Application No. PCT/KR2018/000350, dated Apr. 26, 2018.
Office Action issued in Chinese Application No. 2018800172042, dated Mar. 3, 2021.
Office Action issued in corresponding Indonesian Application No. P00201906980, dated Apr. 1, 2021.
Office Action issued in corresponding KR Application No. 10-2017-0071843, dated Dec. 9, 2021 and English translation, 11 pages.

* cited by examiner

1000

5000

270

370

470

740

740

Adhesive-type insect trap

ADHESIVE-TYPE INSECT TRAP HAVING A MAIN BODY FOR GUIDING AND STOPPING MOVEMENT OF AN ADHESIVE SHEET

RELATED APPLICATIONS

The present application is a U.S. national stage application under 35 U.S.C. § 371 of PCT Application No. PCT/KR2018/000268 filed Jan. 5, 2018, which claims priority to Korean Application Nos. 10-2017-0003381 filed Jan. 10, 2017, 10-2017-0071843 filed Jun. 8, 2017, 10-2017-0089813 filed Jul. 14, 2017, and 10-2017-0097770 filed Aug. 1, 2017, all of which are hereby incorporated in their entirety by reference as set forth herein.

TECHNICAL FIELD

The present disclosure relates to an adhesive-type insect trap and, more particularly, to an adhesive-type insect trap adapted to collect insects by luring insects using a light source and causing insects attached thereto. The present disclosure further relates to an adhesive-type insect trap having a main body for guiding and stopping movement of an adhesive sheet.

RELATED ART

Generally, flying insects such as flies, mosquitoes, and moths are infectious vectors that carry various kinds of germs, and cause direct or indirect damage to humans or crops.

Although various pesticides and insecticides have been used to eliminate such harmful insects, such pesticides and insecticides are harmful to a human body and cause ecological imbalance. As an alternative, various methods, such as development of biodegradable insecticides, use of natural enemies or pheromones, and application of insecticide after attraction of insects, have been studied.

As an example of application of insecticide after attraction of insects, there is a so-called electric insecticidal apparatus in which an infrared (IR) heater lamp is mounted inside a main body of the apparatus in order to attract insects exhibiting positive phototaxis to move from the periphery to bright light such that insects attracted to the heater lamp side are electrically charged by heat from the heater lamp. However, due to use of high voltage, the apparatus has problems of high power consumption and risk of electric shock, generating noise and an odor upon electric shock of an insect, and scattering an insect pollutant or a fragment thereof.

In order to solve such problems of the electric insecticidal apparatus, an insect trap using a flypaper-type adhesive sheet has been developed. However, this insect trap has problems in that an insect trapped in the insect trap is seen from the outside, providing an unpleasant feeling to a user, in that a light source mounted on the insect trap has significantly low attraction efficiency, in that the adhesive sheet is likely to adhere to the insect trap upon insertion into the insect trap, or in that the adhesive sheet is easily released after insertion into the insect trap.

SUMMARY

Embodiments of the present disclosure provide an adhesive-type insect trap that collects insects by attracting the insects to move towards the insect trap using a light source and that has high trapping efficiency while preventing the insects from being directly visibly observed from the outside.

Embodiments of the present disclosure provide an adhesive-type insect trap that prevents an adhesive sheet from being attached to the insect trap upon insertion into the insect trap and that allows the adhesive sheet to be secured to a main body of the insect trap after insertion into the insect trap.

Embodiments of the present disclosure provide an adhesive-type insect trap that includes a photocatalyst generating deodorization effect. Embodiments of the present disclosure provide an adhesive-type insect trap that can generate not only light but also a gas such as carbon dioxide, as an element for attraction of mosquitoes.

Embodiments of the present disclosure provide an adhesive-type insect trap that is provided with a UVC light source capable of sterilizing the interior of the insect trap or killing insects trapped by an adhesive sheet.

Embodiments of the present disclosure provide an adhesive-type insect trap that is provided with a camera capable of observing or photographing insects collected therein. Embodiments of the present disclosure provide an adhesive-type insect trap that is provided with a sensor for detecting the kind of insect trapped therein, an area of an adhesive sheet trapping insects, brightness of the adhesive sheet, an ambient temperature or illuminance of a light source, the intensity of light emitted from the light source, presence of the adhesive sheet in the insect trap, attachment of a cover to the insect trap, and the like, for adjusting the intensity of light emitted from the light source, or for supplying electric power to the light source depending upon the presence of the adhesive sheet in the insect trap or the attachment of the cover to the insect trap.

Embodiments of the present disclosure provide an adhesive-type insect trap that further includes an insect attractant spray or includes an insect attractant contained in an adhesive sheet to improve insect attraction efficiency.

BRIEF DESCRIPTION OF DRAWINGS

FIG. 30 shows a guide member according to one embodiment of the present disclosure, where

DETAILED DESCRIPTION OF EMBODIMENTS

Figure 1:
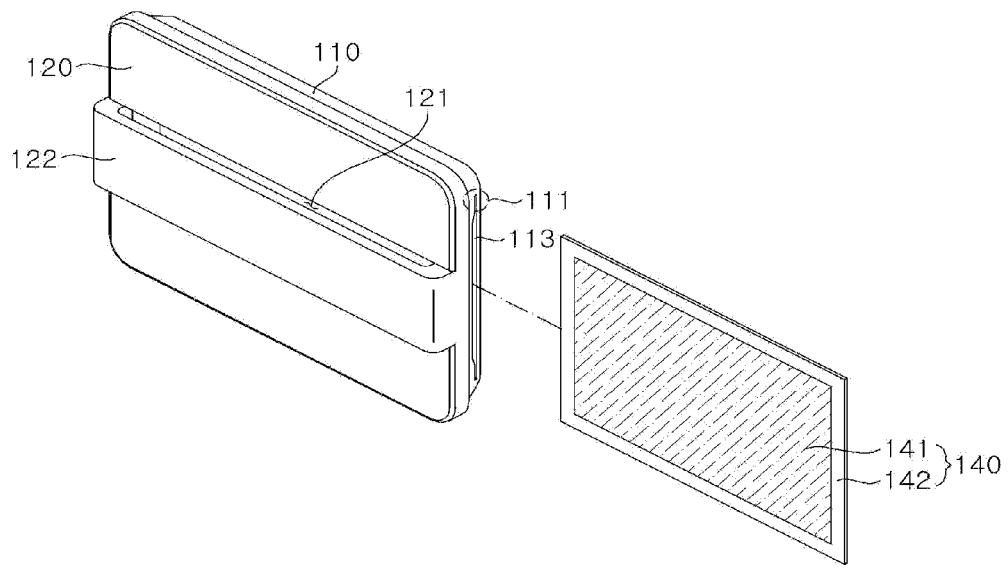
FIG. 1 and FIG. 2 show an adhesive-type insect trap according to one embodiment of the present disclosure.

It should be understood that the present disclosure may be embodied in different ways and is not limited to the following embodiments, which are provided for complete disclosure and thorough understanding of the present disclosure by those skilled in the art.

Herein, when an element such as a layer or a film is referred to as being placed "on" or "under" another element, it can be directly placed "on" or "under" the other element, or intervening element(s) may be present therebetween. Herein, spatially relative terms such as "upper" and "lower" are defined with reference to the accompanying drawings. Thus, it will be understood that the term "upper surface" can be used interchangeably with the term "bottom surface".

Like components will be denoted by like reference numerals throughout the accompanying drawings. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

As used herein, the term "insect" may refer to various kinds of flying insects, particularly flies, without being limited thereto, and a light source may be selected from various kinds of light sources, for example, a UV LED, without being limited thereto.

In addition, as used herein, the term "guide unit" may refer to at least one of a guide groove, a guide rail, and a guide member described below.

One aspect of the present disclosure provides an adhesive-type insect trap including: a main body having an adhesive sheet insertion hole; a light source mount disposed on the main body; and a cover detachably attached to the main body and having a through-hole formed in at least a portion thereof, wherein the adhesive sheet includes a flypaper piece and a sheet, and the main body includes a guide unit guiding the adhesive sheet and further includes an adhesive sheet support supporting the adhesive sheet.

In one embodiment, at least one of the flypaper piece and the sheet may allow light emitted from a light source mounted on the light source mount to pass therethrough. In one embodiment, the sheet may allow light emitted from a light source mounted on the light source mount to pass therethrough and the flypaper piece may be disposed in a lattice shape on the sheet.

In one embodiment, at least one of the flypaper piece and the sheet may have a punching hole. In one embodiment, each of the flypaper piece and the sheet may have a punching hole and the punching hole formed on the flypaper piece may at least partially overlap the punching hole formed on the sheet. In one embodiment, the adhesive sheet may include a flypaper piece and a reflective sheet. In one embodiment, the flypaper piece may allow light emitted from a light source mounted on the light source mount to pass therethrough. In one embodiment, the flypaper piece may be disposed in a lattice shape on the sheet.

In one embodiment, the main body and the adhesive sheet may include magnet members disposed to face each other and having opposite polarities, respectively.

In one embodiment, the adhesive-type insect trap may further include a sensor detecting at least one of the kind of insect trapped on the adhesive sheet, an area of the adhesive sheet trapping insects, brightness of the adhesive sheet, an ambient temperature of the light source, the intensity of light emitted from the light source, ambient illuminance of the insect trap, insertion of the adhesive sheet into the insect trap, and attachment of the cover to the insect trap.

In one embodiment, the adhesive-type insect trap may further include a UVC (ultraviolet C) light source emitting UVC light. In one embodiment, the guide unit may include a guide rail, and the guide rail and the adhesive sheet may include magnet members disposed to face each other and having opposite polarities, respectively. In one embodiment, the guide unit may include guide members and at least two guide members may be disposed on opposite surfaces of the main body with reference to the adhesive sheet, respectively. In one embodiment, the guide unit may include a guide rail and the guide member may include at least two plates having different heights from a main body bottom. In one embodiment, among the at least two plates of the guide member, a plate near the adhesive sheet insertion hole may have the greatest height.

In one embodiment, the guide member may include a slanted portion disposed between the plural plates and the slanted portion may have a larger inclination than an angle defined between a plate having the lowest height in one guide member and the main body bottom. In one embodiment, the main body may include a stopper unit stopping movement of the adhesive sheet guided into the main body. In one embodiment, the stopper unit may include a stopper plate and a tongue portion, and the tongue portion may be slanted in a direction in which the adhesive sheet insertion hole is disposed. In one embodiment, the tongue portion may include a convexly round shape in the direction in which the adhesive sheet insertion hole is disposed.

In one embodiment, the adhesive sheet may be guided to a space between the stopper plate and a main body bottom along a slanted surface of the tongue portion slanted in the direction in which the adhesive sheet insertion hole is disposed. In one embodiment, the adhesive sheet and the stopper plate may include magnet members disposed to face each other and having opposite polarities, respectively. In one embodiment, the cover may include at least one cover protrusion protruding in a direction in which the adhesive sheet is disposed. In one embodiment, the cover protrusion may include a section having an area gradually decreasing in a direction from the cover to the main body bottom.

In one embodiment, a region of the cover protrusion having the smallest cross-sectional area may be disposed at a distal end of the cover protrusion closer to the main body bottom than the cover. In one embodiment, the cover may include a through-hole blocking structure blocking at least a portion of the through-hole, the through-hole blocking structure may include a region concavely depressed towards an interior of the cover, and the cover protrusion may be disposed in the region of the through-hole blocking structure concavely depressed towards the interior of the cover.

In one embodiment, the adhesive-type insect trap may further include a second sensor including a light reception sensor and a light emission sensor to prevent electric power from being supplied to a light source mounted on the light source mount when the adhesive sheet is not inserted into the main body to reach a predetermined location therein, wherein the stopper unit extends from a main body bottom, at least one of the light reception sensor and the light emission sensor is disposed on the main body bottom, and the light emission sensor disposed on the main body bottom to face the light reception sensor or the light reception sensor disposed on the main body bottom to face the light emission sensor is provided to the stopper unit.

In one embodiment, the stopper unit may include a stopper plate and a tongue portion slanted in a direction in which the adhesive sheet insertion hole is disposed, and the light emission sensor disposed on the main body bottom to face the light reception sensor or the light reception sensor disposed on the main body bottom to face the light emission sensor may be provided to the stopper plate. In one embodiment, the guide member may include an end wall disposed in a width direction of the plate to stop movement of the adhesive sheet and extending from the main body bottom.

In one embodiment, the main body may include a signal transmission unit and a light reception unit disposed along an outer periphery of the adhesive sheet inserted into the main body, wherein the signal transmission unit sends a signal and the signal reception unit receives the signal sent from the signal transmission unit. In one embodiment, the signal transmission unit and the signal reception unit may be disposed to face each other, and the signal reception unit may receive a signal sent from the corresponding signal transmission unit.

In one embodiment, the signal transmission unit may include a first signal transmission unit, a second signal transmission unit, . . . , and an $n^{th}$ signal transmission unit, and the signal reception unit may include a first signal reception unit, a second signal reception unit, . . . , and an $n^{th}$ signal reception unit corresponding to the first to nth signal transmission units, respectively, to detect information on insects passing through or trapped in spaces between the first signal transmission unit and the first signal reception unit, between the second signal transmission unit and the second signal reception unit, . . . , and between the $n^{th}$ signal transmission unit and the $n^{th}$ signal reception unit.

In one embodiment, the information on insects may include the number of insects trapped therein.

Another aspect of the present disclosure provides an adhesive-type insect trap including: a main body having an adhesive sheet insertion hole; a light source mount disposed on the main body; and a cover detachably attached to the main body and having a through-hole formed in at least a portion thereof, wherein the adhesive sheet includes a flypaper piece and a sheet, and the main body includes a guide unit guiding the adhesive sheet and further includes a securing member securing the adhesive sheet inserted into the main body.

In one embodiment, the flypaper piece may be disposed to be separated from an outer peripheral surface of the sheet into the sheet by a predetermined distance and the securing member may press the sheet.

In one embodiment, the securing member may include: a rotating portion; a connecting portion connected to the rotating portion; a bent portion extending in a bent shape from the connecting portion and imparting resilient force to the securing member; and a pressing portion extending from the bent portion and applying compressive force to the sheet.

In one embodiment, the bent portion may apply resilient force in a ∧ shape or in a V shape so as to allow the pressing portion to generate compressive force to a plurality of adhesive sheets inserted into the main body.

In one embodiment, the securing member may further include a tongue portion extending from the pressing portion and having a distal end separated from the sheet by a predetermined distance. In one embodiment, the adhesive sheet may include a plurality of flypaper pieces. In one embodiment, the plurality of flypaper pieces may be stacked one above another in a height direction of the adhesive sheet. In one embodiment, each of the flypaper pieces stacked one above another may include an adhesive surface on an upper surface thereof, such that, when a flypaper piece adjoining a lower surface of another flypaper piece is separated from the other flypaper piece, the adhesive surface of the flypaper piece separated from the lower surface of the other flypaper piece is exposed. In one embodiment, the flypaper piece may further include a gripper including a region free from an adhesive liquid.

A further aspect of the present disclosure provides an adhesive-type insect trap including: a main body having an adhesive sheet insertion hole; a light source mount disposed on the main body; and a cover detachably attached to the main body and having a through-hole formed in at least a portion thereof, wherein the adhesive sheet includes a flypaper piece and a sheet; the main body includes a guide unit guiding the adhesive sheet; the adhesive sheet includes a first securing member at least partially disposed thereon and the main body includes a second securing member disposed to face the first securing member such that at least a portion of the adhesive sheet is brought into tight contact with a main body bottom by interaction between the first securing member and the second securing member.

In one embodiment, at least one of the first securing member and the second securing member may generate magnetic force. In one embodiment, the second securing member may include a first sensor to prevent electric power from being supplied to a light source mounted on the light source mount when the adhesive sheet is not inserted into the main body to reach a predetermined location therein. In one embodiment, the first sensor may include a magnetic sensor generating a ground signal. In one embodiment, the adhesive-type insect trap may further include a second sensor to prevent electric power from being supplied to a light source mounted on the light source mount when the adhesive sheet is not inserted into the main body to reach a predetermined location therein.

In one embodiment, the second sensor may include a light reception sensor and a light emission sensor, and at least one of the light reception sensor and the light emission sensor may be disposed on the main body bottom.

Hereinafter, embodiments of the present disclosure will be described in more detail with reference to the accompanying drawings.

FIG. 1 shows an adhesive-type insect trap according to one embodiment of the present disclosure. Referring to FIG. 1, an adhesive-type insect trap 1000 includes a main body 110 and a cover 120, and may receive an adhesive sheet 140 inserted therein. The main body 110 may have a shape corresponding to a shape of the adhesive sheet 140 guided into the main body 110 instead of having a particular shape. For example, the main body 110 may include a casing having a hexahedral shape in which an adhesive sheet 140 having a plate shape is guided, and may be formed of a plastic material generally used in the art in order to allow the insect trap to be used indoors or outdoors for a long period of time while preventing excessive increase in manufacturing costs, without being limited thereto.

In addition, the main body 110 includes an adhesive sheet insertion hole 113 formed on a front surface of the main body 110 such that the adhesive sheet 140 can be inserted in an upright posture into the main body 110 in a vertically sliding manner or in a horizontally sliding manner, and a guide groove 111 formed on at least one side of the adhesive sheet insertion hole 113 to guide the adhesive sheet 140. The guide groove 111 may be configured to receive an edge of the adhesive sheet 140 inserted into the main body 110, may have a thickness corresponding to a thickness of the adhesive sheet 140 to allow easy insertion and separation of the adhesive sheet 140 and a depth corresponding to a length preventing a flypaper piece 141 of the adhesive sheet 140 from contacting the main body 110. By way of example, the adhesive sheet insertion hole 113 may have an open shape or a closed shape opened or closed by a door (not shown), which may have any shape and may be configured to block or open at least a portion of the adhesive sheet insertion hole 113.

The cover 120 may have any shape without being limited to a particular shape and may be detachably attached to a front side of the main body 110. The cover 120 may have a through-hole 121 formed in at least a portion thereof to allow insects to pass therethrough, may be formed of a material allowing light emitted from a light source 170 mounted on a light source mount 130 to pass therethrough, and may have a roughened surface or may include a separate cover sheet attached to or spaced apart from a front side or a rear side of the cover 120 to allow refraction or diffusion of the light. The cover 120 may be rotatably disposed on the main body 110 such that a user can change the location of the cover 120 depending upon user environment. Further, the cover 120 may be detachably attached to the main body 110 through sliding movement or by a magnet in order to prevent damage to components of the adhesive-type insect trap 1000 such as the adhesive sheet 140 and the like due to application of excessive force to the cover 120 to separate the cover 120 from the main body 110 by a user. Further, the cover 120 may be connected to the main body 110 through a ring, a chain or a string formed of a stretchable material. Alternatively, the cover 120 may be secured at one side thereof to the main body 110 and detachably coupled at the other side thereof to the main body 110 to prevent the cover 120 from being completely separated from the main body 110.

By way of example, at least a portion or the entirety of the cover 120 may be formed of a light transmissive material. For example, a portion of the cover 120 through which light emitted from the light source 170 passes may comprise polycarbonate (PC), polyethylene terephthalate (PET), methacrylate-styrene (MS), poly(methyl methacrylate) (PMMA), or the like, and may have at least one of transparent, translucent and opaque colors.

The cover 120 may have a through-hole blocking structure 122 adapted to block at least a portion of the through-hole 121. The through-hole blocking structure 122 may have any shape capable of blocking at least a portion of the through-hole 121. In some embodiments, the through-hole blocking structure 122 may be integrally formed with the cover 120. In other embodiments, the through-hole blocking structure 122 may be detachable from the cover 120. In addition, the through-hole blocking structure 122 may extend from the cover 120 to protrude outward from the cover 120 or may be formed by a convex or concave portion of the cover 120. By way of example, referring to FIG. 1, the through-hole blocking structure 122 may be realized by a protruded portion relative to the cover 120.

That is, the adhesive-type insect trap 1000 has the through-hole blocking structure 122 adapted to block the adhesive sheet 140 from being visible from the outside, thereby preventing insects attached to the adhesive sheet 140 from being observed from the outside.

The adhesive sheet 140 may include a flypaper piece 141 applied to or coated onto a sheet 142. For example, the flypaper piece 141, which is a pressure sensitive adhesive material, is applied to or coated on one surface of a paper sheet to trap insects attached to the adhesive material. Here, instead of being applied to or coated onto the entire surface of the sheet 142, the flypaper piece 141 may be partially applied to or coated onto the sheet 142 to expose at least a portion of the sheet 142 such that a user can easily replace the adhesive sheet without a separate gripper formed on the sheet 142 while preventing the flypaper piece 141 from being adhered to the adhesive sheet insertion hole 113 or the guide groove 111.

Figure 2:
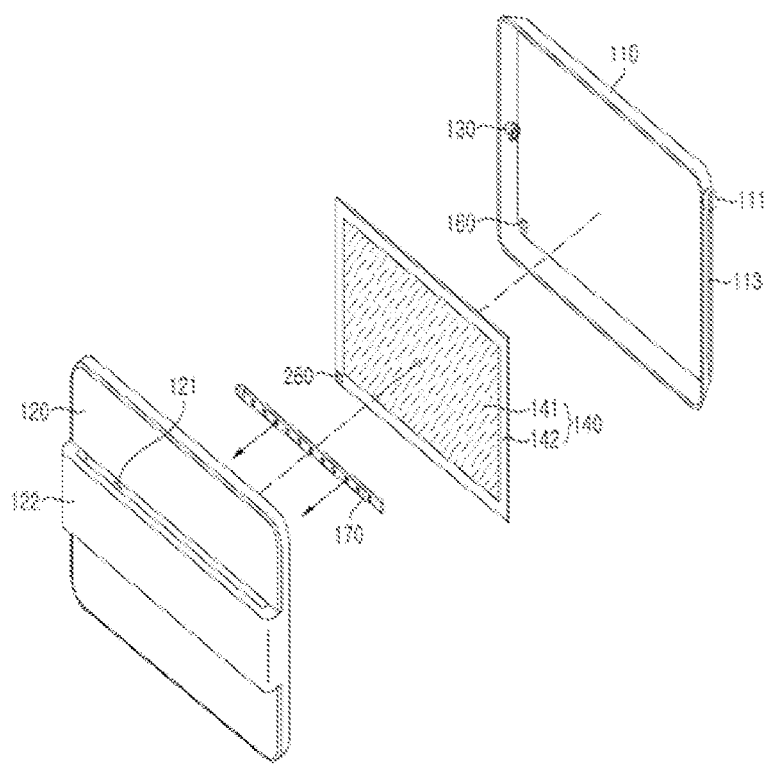

Referring to FIG. 2, the main body 110 and the adhesive sheet 140 may include magnet members 160, 260 disposed to face each other and having opposite polarities, respectively. That is, the adhesive sheet 140 may be prevented from being separated from the main body even upon rotation of an adhesive-type insect trap 2000 after installation of the adhesive sheet 140 to the main body 110 by a user.

Referring again to FIG. 2, the adhesive-type insect trap 2000 may further include the light source mount 130 received in the main body 110. The light source mount 130 is provided with the light source 170, which not only acts as a lighting fixture but also emits light for attraction of insects or UVC for sterilization of insects or bacteria in the insects collected in the insect trap. The light source mount 130 may include a socket and may be disposed in any direction including a longitudinal direction and a transverse direction.

The light source 170 emits light having a wavelength capable of attracting insects and the main body 110 may include at least one light source therein. For example, the light source 170 may emit UV light having a wavelength of 350 nm to 400 nm, at which the light source 170 can efficiently attract insects exhibiting positive phototaxis to move from the periphery to bright light, thereby improving insect attraction efficiency without providing harmful influence to a user body.

The adhesive sheet 140 may be provided to at least one of a front side, a rear side and lateral sides of the light source mount 130 and may be formed of a transparent material or an opaque material depending upon installation locations of the adhesive sheet 140 and the light source mount 130. For example, when light emitted from the light source 170 is emitted outside the cover 120 after passing through the adhesive sheet 140, both the flypaper piece 141 and the sheet 142 of the adhesive sheet 140 may be formed of a light transmissive material or at least one of the flypaper piece 141 and the sheet 142 may be formed of a light transmissive material, for example, a material having high UV light transmittance, to allow light emitted from the light source 170 to pass therethrough.

Figure 3:
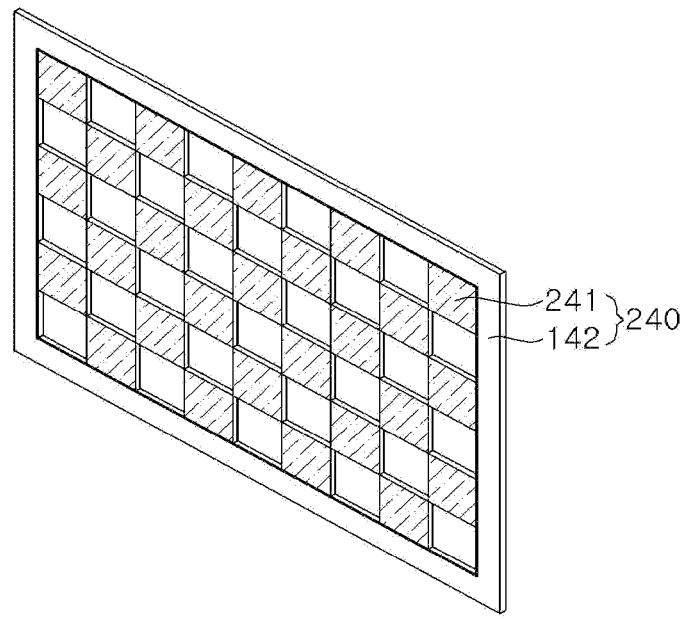
FIG. 3 and FIG. 4 show an adhesive sheet according to embodiments of the present disclosure, respectively.
Figure 4:
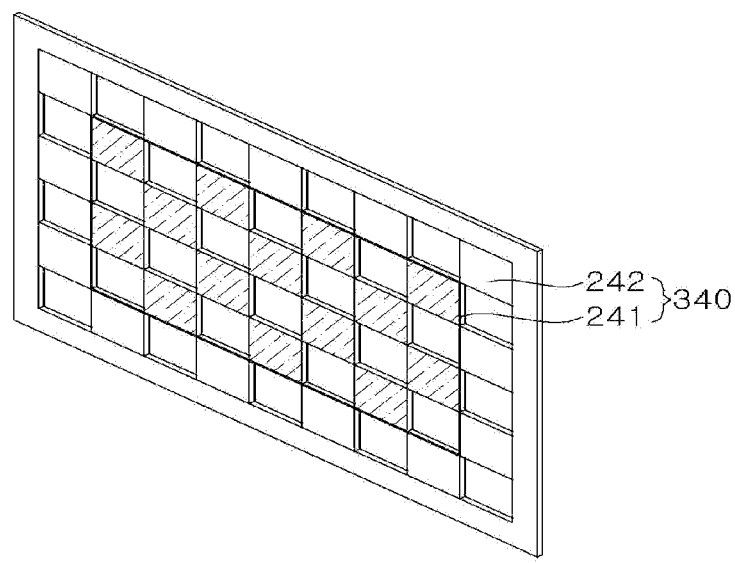

For example, referring to FIG. 3, an adhesive sheet 240 includes a sheet 142 formed of a transparent material and a flypaper piece 241 formed of an opaque material. In this example, the flypaper piece 241 may be disposed in a lattice shape or may be disposed to form punching holes. Alternatively, referring to FIG. 4, in an adhesive sheet 340, both a sheet 242 and the flypaper piece 241 may be disposed in a lattice shape or may be disposed to form punching holes, and the punching holes formed through the sheet 242 and the flypaper piece 241 at least partially overlap each other to allow light emitted from the light source 170 to pass therethrough. Here, each frame of the lattice shape may have a smaller size than insects, for example, flies, and may have a length of 2 mm to 8 mm.

FIG. 5 through FIG. 10 show various embodiments of the light source 170 and the adhesive sheet 140 disposed on an adhesive-type insect trap 3000, 4000, 5000, 6000, 7000 or 8000. In this drawings, the light source 170 is shown instead of the light source mount 130, in order to allow a person having ordinary knowledge in the art to clearly understand arrangement of the light source 170 and the adhesive sheet 140 on each insect trap. The light source 170 may be a sheet light source or a spot light. In FIG. 5 through FIG. 10, a spot light source is shown by way of example.

Figure 5:
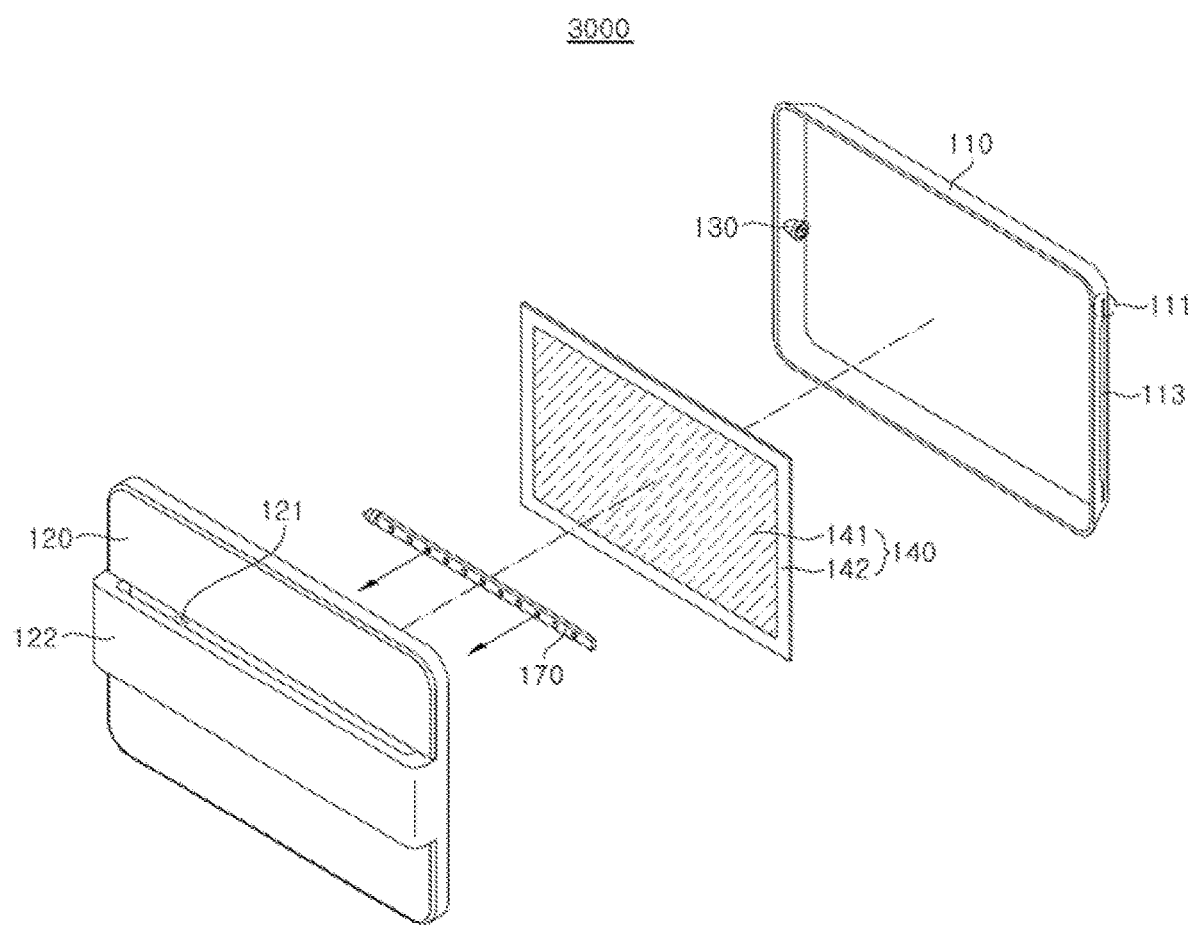
FIG. 5 shows an adhesive-type insect trap having a light source disposed in a space between an adhesive sheet and a cover according to an embodiment of the present disclosure.
Figure 6:
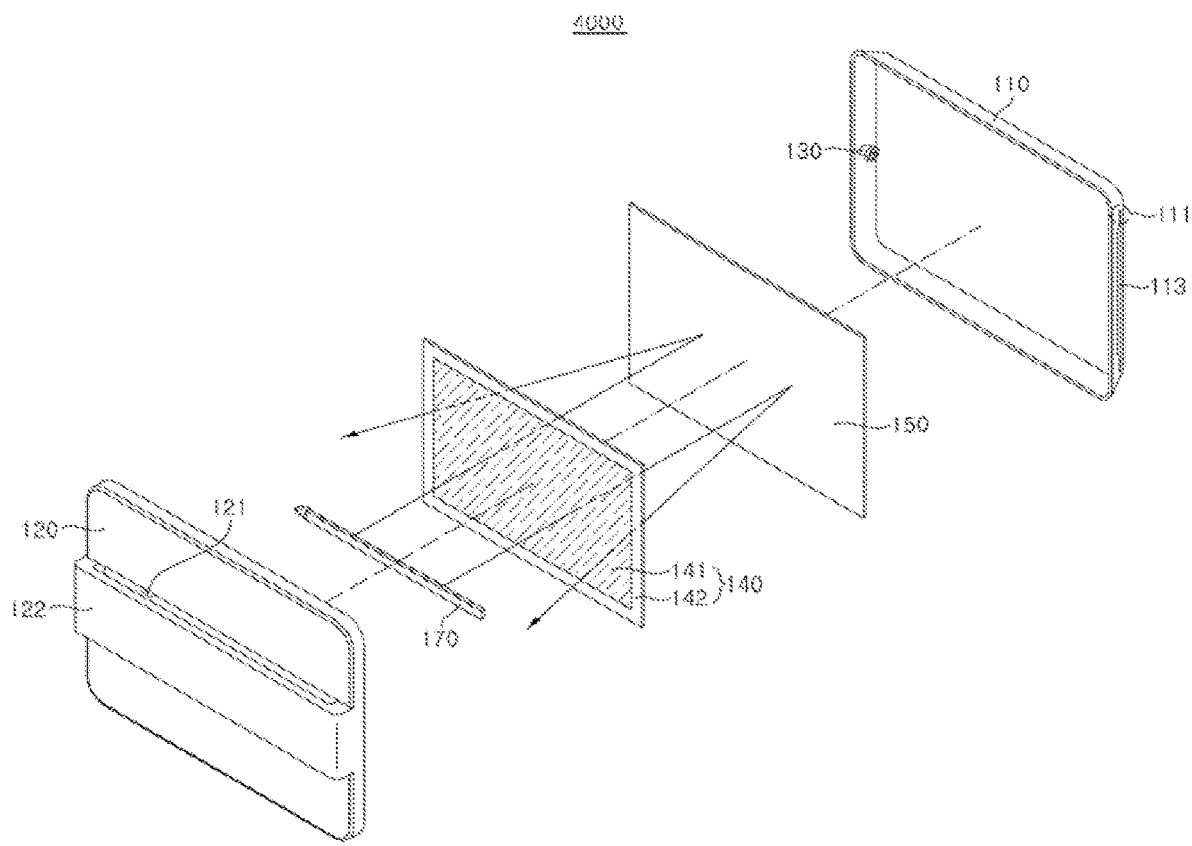
FIG. 6 shows an adhesive-type insect trap having a light source disposed in a space between an adhesive sheet and a cover and having a reflector between the adhesive sheet and a main body according to an embodiment of the present disclosure.
Figure 7:
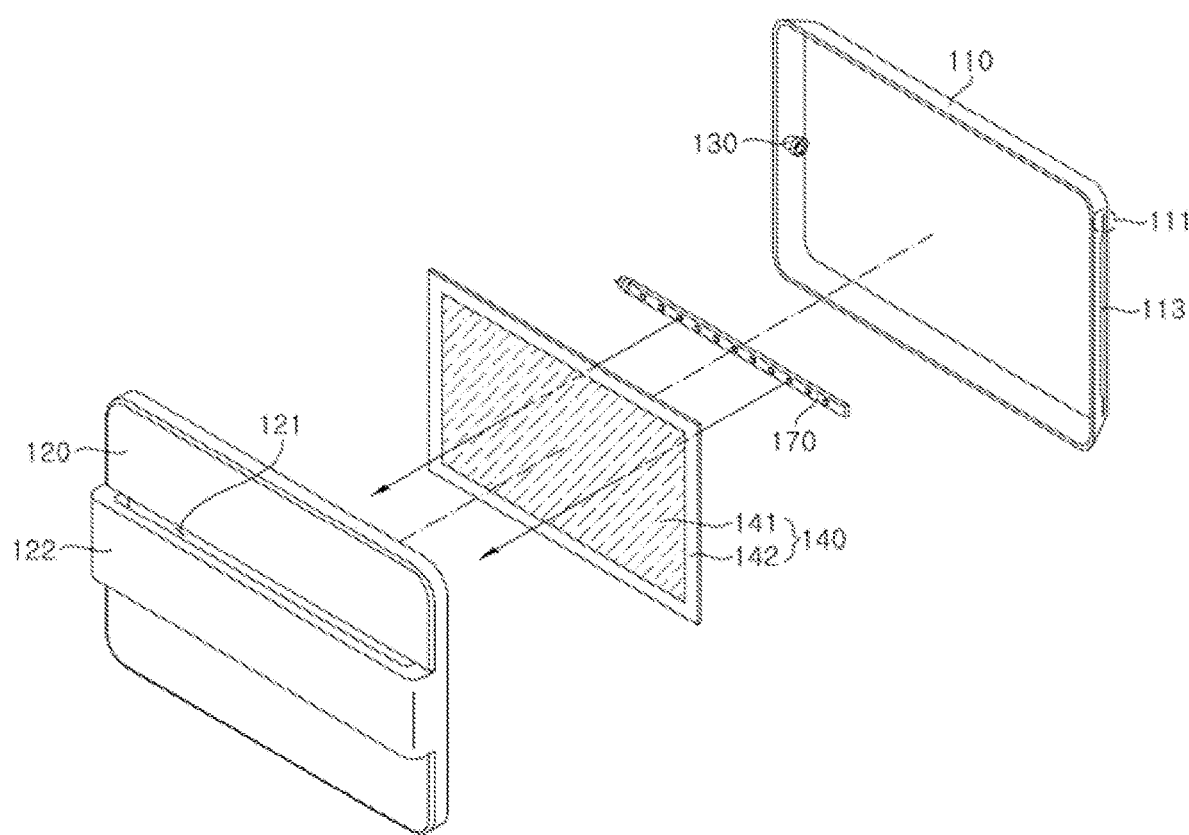
FIG. 7 shows an adhesive-type insect trap having a light source disposed in a space between an adhesive sheet and a main body according to an embodiment of the present disclosure.
Figure 8:
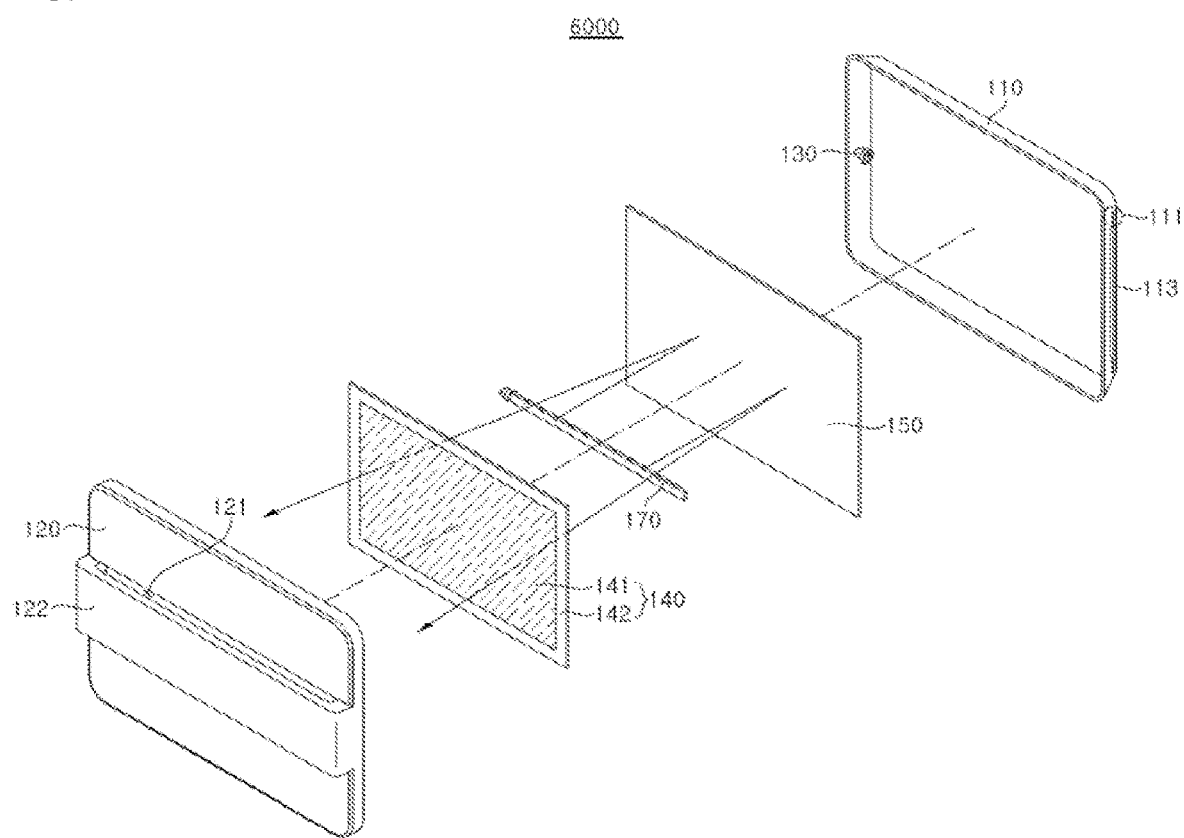
FIG. 8 shows an adhesive-type insect trap having a light source and a reflector between an adhesive sheet and a main body according to an embodiment of the present disclosure.
Figure 9:
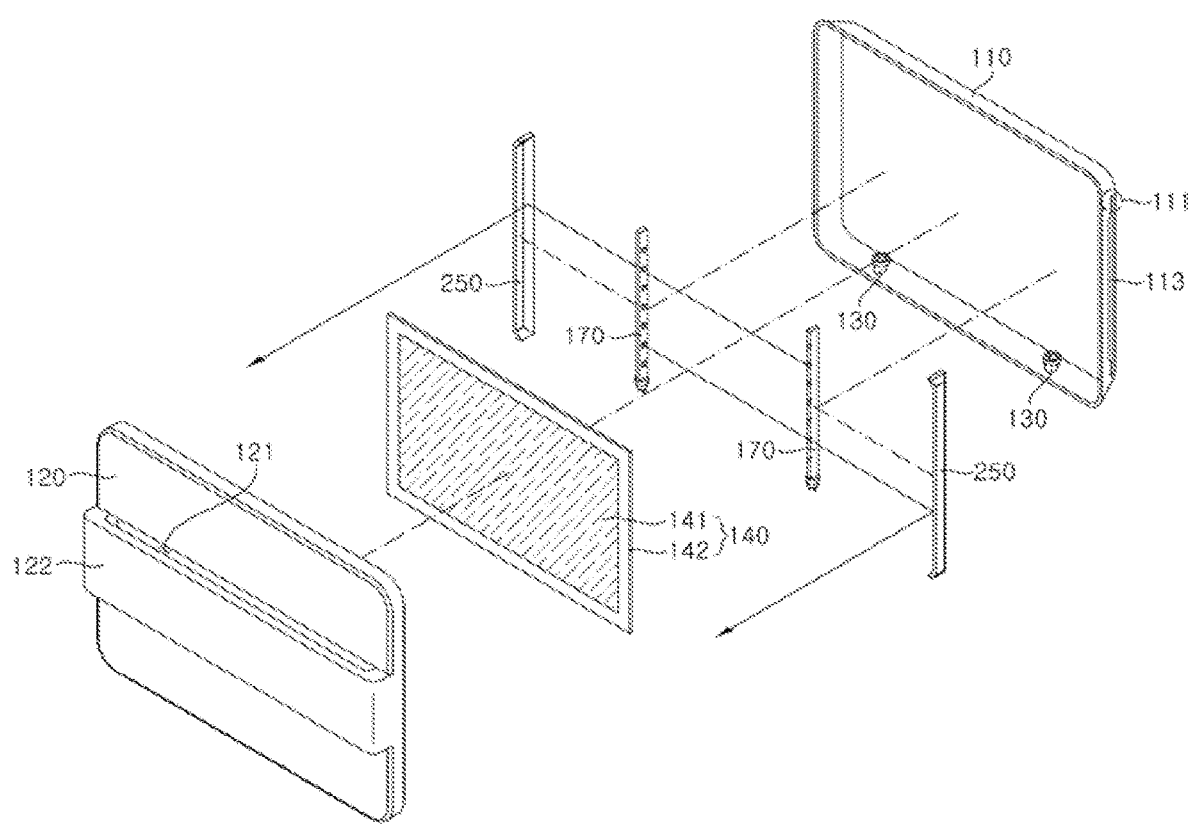
FIG. 9 shows an adhesive-type insect trap having plural light sources according to an embodiment of the present disclosure.
Figure 10:
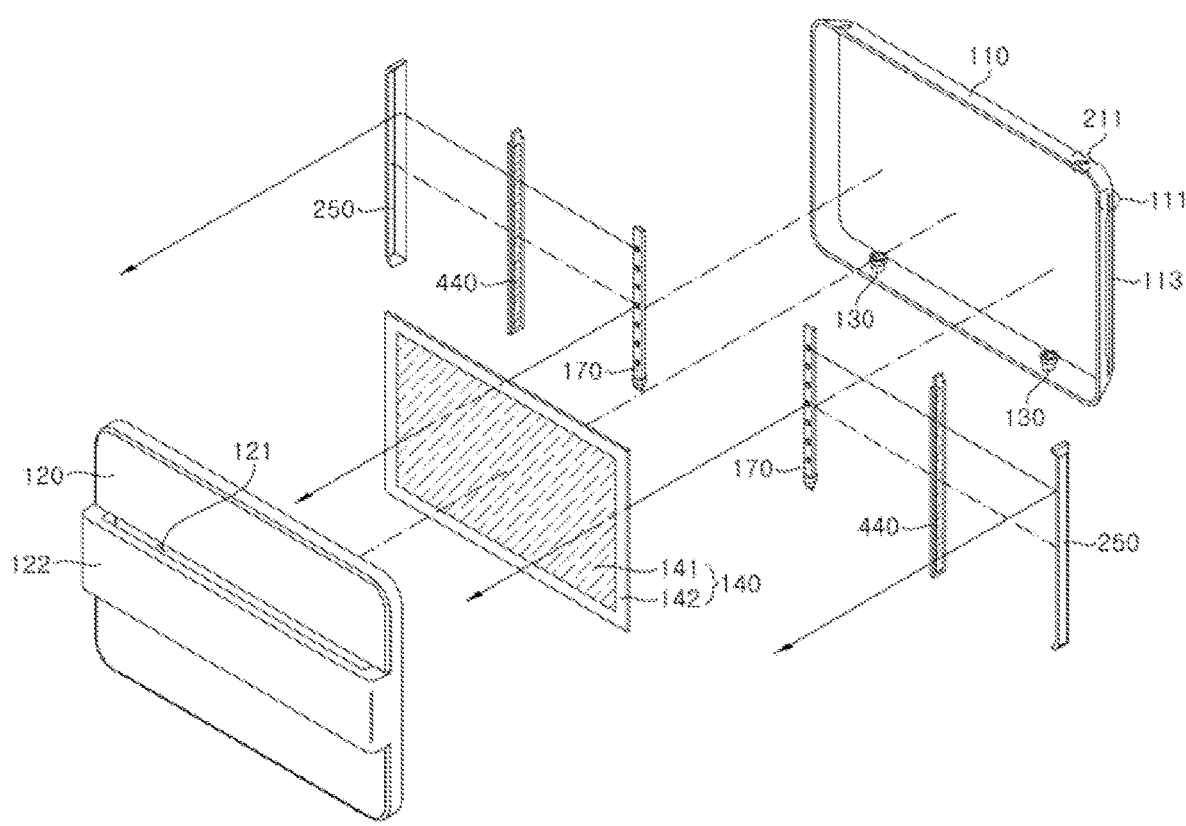
FIG. 10 shows an adhesive-type insect trap having a different light emission direction than the adhesive-type insect trap of FIG. 9 and having additional adhesive sheets according to an embodiment of the present disclosure.

FIG. 5 shows an adhesive-type insect trap having a light source disposed in a space between an adhesive sheet and a cover according to an embodiment of the present disclosure. FIG. 6 shows an adhesive-type insect trap having a light source disposed in a space between an adhesive sheet and a cover and having a reflector between the adhesive sheet and a main body according to an embodiment of the present disclosure. FIG. 7 shows an adhesive-type insect trap having a light source disposed in a space between an adhesive sheet and a main body according to an embodiment of the present disclosure. FIG. 8 shows an adhesive-type insect trap having a light source and a reflector between an adhesive sheet and a main body according to an embodiment of the present disclosure. FIG. 9 shows an adhesive-type insect trap having plural light sources according to an embodiment of the present disclosure. FIG. 10 shows an adhesive-type insect trap having a different light emission direction than the adhesive-type insect trap of FIG. 9 and having additional adhesive sheets according to an embodiment of the present disclosure.

Referring to FIG. 5, in the adhesive-type insect trap 3000, the light source 170 may be disposed in a space between the adhesive sheet 140 and the cover 120 such that light emitted from the light source 170 is directed towards the cover 120, and the adhesive sheet 140 may be formed to allow or prevent light transmission therethrough. The adhesive-type insect trap 3000 does not require additional reflectors 150, 250, a reflective sheet 143, or the flypaper pieces 141, 241, thereby enabling reduction in manufacturing costs.

Referring to FIG. 6, the adhesive-type insect trap 4000 may further include a reflector 150 disposed between the adhesive sheet 140 and the main body 110, in which the light source 170 may be disposed in a space between the adhesive sheet 140 and the cover 120 such that light emitted from the light source 170 is directed towards the main body 110. As described above, the adhesive sheet 140 may be formed of a light transmissive material or may partially have a lattice shape to allow light emitted from the light source 170 to pass therethrough. Insects, particularly flies, tend to be more strongly attracted to refracted or diffused light than to direct light. Thus, the adhesive-type insect trap 4000 is configured to allow light emitted from the light source 170 to pass through the adhesive sheet 140 at least once, instead of directly passing through the cover, thereby improving insect attraction efficiency with decoy light.

Referring to FIG. 7, the adhesive-type insect trap 5000 includes the light source 170 disposed in a space between the adhesive sheet 140 and the main body 110 such that light emitted from the light source 170 is directed towards the adhesive sheet 140 and the cover 120 to be refracted or spread instead of directly irradiating insects, thereby improving insect attraction efficiency with decoy light.

Referring to FIG. 8, the adhesive-type insect trap 6000 may further include the reflector 150 between the light source 170 and the main body 110, in which the light source 170 may be disposed in a space between the adhesive sheet 140 and the reflector 150 such that light emitted from the light source 170 is directed towards the reflector 150. With the structure that prevents light from directly reaching the adhesive sheet 140 and insects while allowing the light to be refracted or spread, the flypaper piece applied to the adhesive sheet 140 can be prevented from being deformed by light or heat while improving insect attraction efficiency with decoy light.

The adhesive-type insect trap 7000 or 8000 may include a plurality of light sources 170, which may be disposed in a direction in which the flypaper piece 141 of the adhesive sheet 140 is disposed, in an opposite direction thereto, or on a side surface. By way of example, referring to FIG. 9, in the adhesive-type insect trap 7000, the plural light sources 170 are disposed to face each other in opposite directions such that light emitted from one light source 170 is directed to another light source 170 disposed in an opposite direction to the one light source 170, and each reflector 250 may be disposed in an opposite direction to a direction in which each light source 170 emits light. By way of example, the reflector 250 includes a flat reflective surface and a bent portion formed at each side of the reflective surface except for sides of the reflective surface adjacent to the cover to allow light to be directed towards the cover. By way of example, the adhesive-type insect trap 7000 includes the plurality of light sources 170 disposed in a space between the adhesive sheet 140 and the main body 110, and allows light emitted from each of the light sources 170 to sequentially pass through the adhesive sheet 140 and the cover 120 after being reflected by the reflector 250 disposed at a rear side of the light source 170 disposed in an opposite direction thereto, thereby improving insect attraction efficiency through refraction and diffusion of light.

Referring to FIG. 10, the adhesive-type insect trap 8000 has a different light emission direction than the adhesive-type insect trap 7000 shown in FIG. 9 and may further include additional adhesive sheets 440. For example, the adhesive-type insect trap 8000 may further include the adhesive sheets 440, each of which is disposed between the light source 170 and the reflector 250 along a guide groove 211 formed on the main body 110, such that each of the light sources 170 emits light towards the reflector 250 adjacent thereto and the adhesive sheet 140 disposed corresponding to the front side of the main body 110. That is, the adhesive-type insect trap 8000 allows light emitted from the light sources 170 to be refracted and spread, thereby improving insect attraction efficiency with decoy light, and is provided with the adhesive sheets 440 not only at the front side of the main body 110 but also at lateral sides thereof, thereby improving insect trapping efficiency and capacity.

On the other hand, the adhesive-type insect trap 3000, 4000, 5000, 6000, 7000 or 8000 shown in FIG. 5 through FIG. 10 may include the plurality of light sources 170, at least one of which may emit UVC light. Accordingly, the adhesive-type insect trap 3000, 4000, 5000, 6000, 7000 or 8000 according to the embodiments of the disclosure includes a UVC light source disposed to emit UVC light towards the adhesive sheet 140, 240, 340 or 440 and the interior of the adhesive-type insect trap 3000, 4000, 5000, 6000, 7000 or 8000, thereby rapidly killing insects and sterilizing or neutralizing bacteria contained in the insects or generated within the adhesive-type insect trap 3000, 4000, 5000, 6000, 7000 or 8000. In FIG. 5 through FIG. 10, the plurality of light sources 170 is described for convenience of explanation, but different light sources may be used based on different arrangements of a reflector, an adhesive sheet, or other parts of the adhesive-type insect traps.

Figure 11:
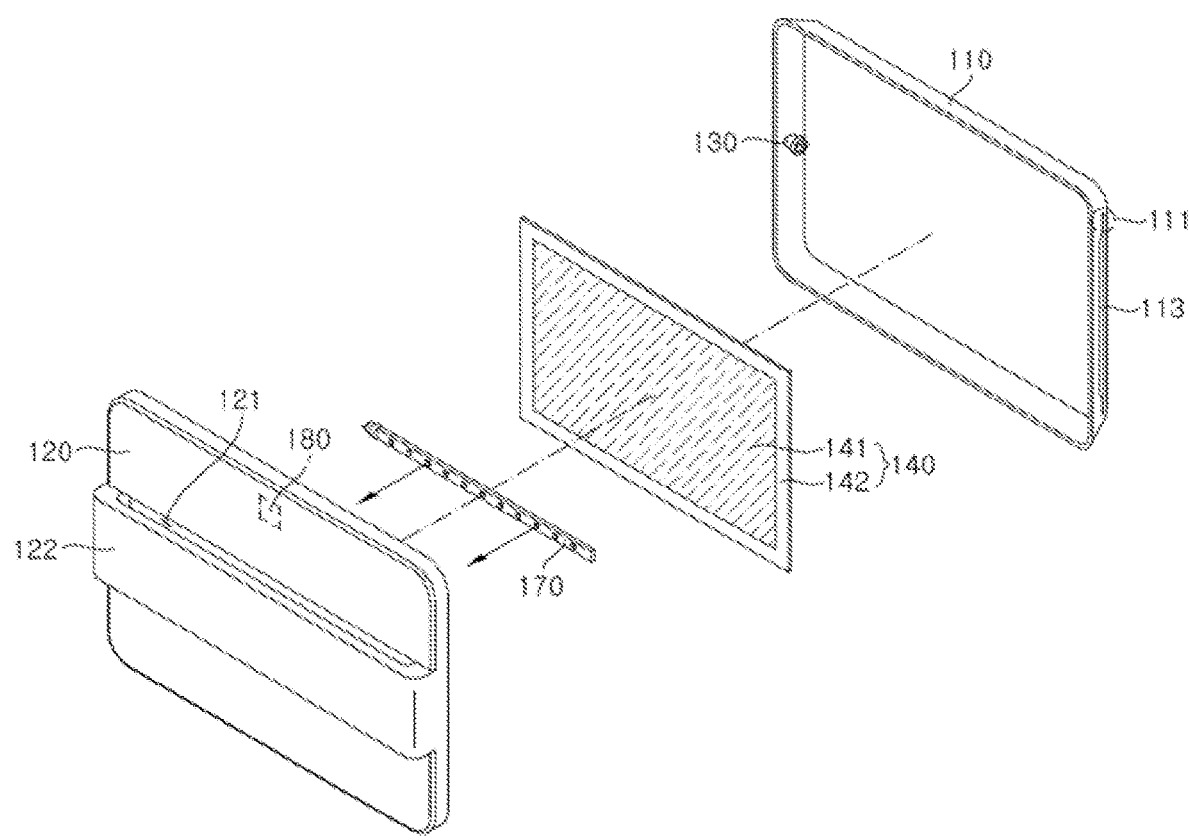
FIG. 11 shows an adhesive-type insect trap having a sensor according to an embodiment of the present disclosure.

Referring to FIG. 11, an adhesive-type insect trap 9000 may further include a sensor 180. The sensor 180 may detect at least one of the kind of insect trapped on the adhesive sheet 140, an area of the adhesive sheet 140 trapping insects, brightness of the adhesive sheet 140, an ambient temperature of the light source 170, the intensity of light emitted from the light source 170, ambient illuminance of the insect trap 9000, insertion of the adhesive sheet 140 into the insect trap, and attachment of the cover 120 to the insect trap 9000.

In one embodiment, the sensor 180 may include a UV sensor capable of detecting the intensity of light emitted from the light source 170 to display an alarm message to a user before lifespan of the light source 170 is finished. The alarm message may be displayed through a separate lamp (not shown) or a separate sound generator (not shown) mounted on the adhesive-type insect trap 9000.

In another embodiment, the sensor 180 may include an illuminance sensor capable of detecting illuminance of surrounding light around the adhesive-type insect trap 9000. For example, the illuminance sensor may be set to have at least one preset illuminance range of the surrounding light and the intensity of light emitted from the light source 170 may be automatically controlled depending upon the illuminance range of the surrounding light. In addition, the adhesive-type insect trap 9000 may further include a luminous intensity regulator (not shown) for regulation of the luminous intensity of the light source 170 to display a desirable luminous intensity of the light source 170 depending upon the illuminance range such that a user can manually regulate the luminous intensity. That is, the adhesive-type insect trap 9000 controls the light source 170 to emit light having suitable intensity for insect attraction, thereby enabling efficient power consumption.

In a further embodiment, the adhesive-type insect trap 9000 may further include a temperature sensor (not shown). The temperature sensor may detect heat generated from the light source 170 mounted on the adhesive-type insect trap 9000 to stop power supply to the light source 170 when the temperature increases above a preset temperature.

In yet another embodiment, the adhesive-type insect trap 9000 may include a magnetic sensor for detecting whether the adhesive sheet 140 is inserted into the main body and whether the cover 120 is attached thereto to display an alarm message to a user when the adhesive sheet 140 is incompletely inserted or the cover 120 is incompletely attached to the main body 110.

In yet another embodiment, the adhesive-type insect trap 9000 may include a limit sensor. The limit sensor may permit power supply to the light source 170 when the adhesive sheet 140 is inserted into the main body 110 or the cover 120 is attached to the main body 110, and may stop power supply to the light source or display an alarm message to a user, as described above, when the adhesive sheet 140 is incompletely inserted or the cover 120 is incompletely attached to the main body 110.

In yet another embodiment, the adhesive-type insect trap 9000 may include a photosensor for detecting inflow of insects into the main body. When the insects enter the adhesive-type insect trap 9000, the photosensor may indicate an alarm message to a user, as described above, or supply power to a camera configured to observe insects trapped therein, described below.

Figure 12:
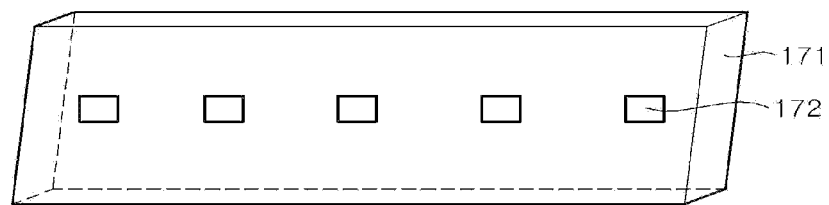
FIG. 12 shows a light source having a single support member according to an embodiment of the present disclosure.
Figure 13:
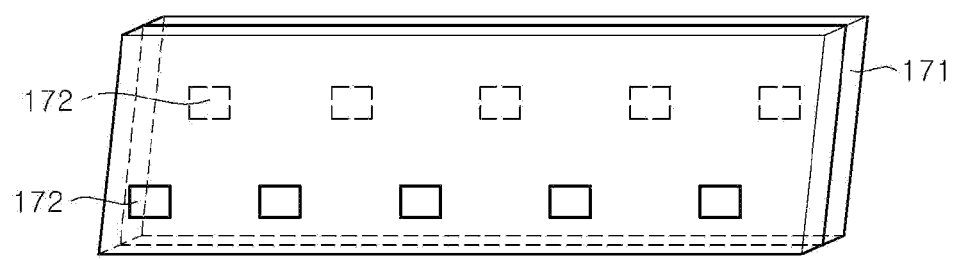
FIG. 13 shows a light source having a stack of support members according to an embodiment of the present disclosure.
Figure 14:
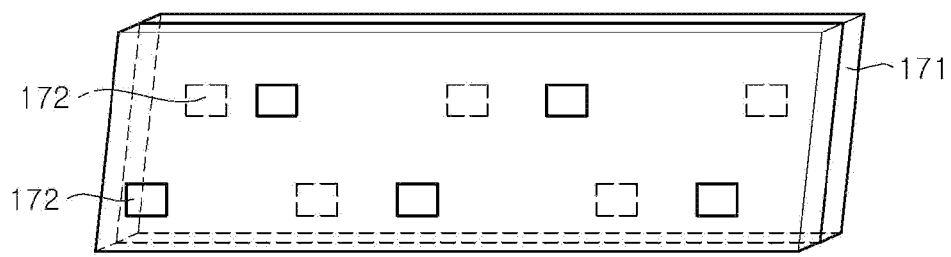
FIG. 14 shows a light source having a different arrangement of light emitting diodes from FIG. 13 according to an embodiment of the present disclosure.
Figure 15:
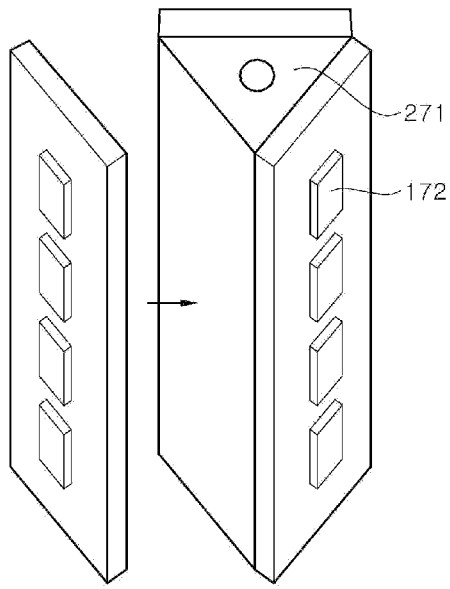
FIG. 15 shows a light source mounted on a polygonal column-shaped support member according to an embodiment of the present disclosure.
Figure 16:
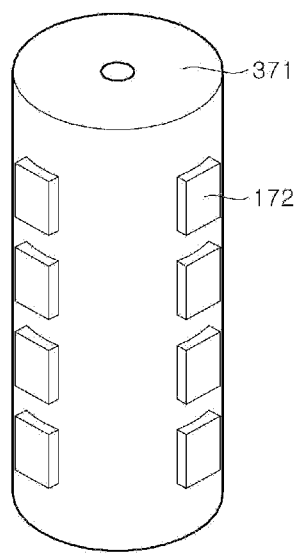
FIG. 16 shows a light source mounted on a cylindrical support member according to an embodiment of the present disclosure.
Figure 17:
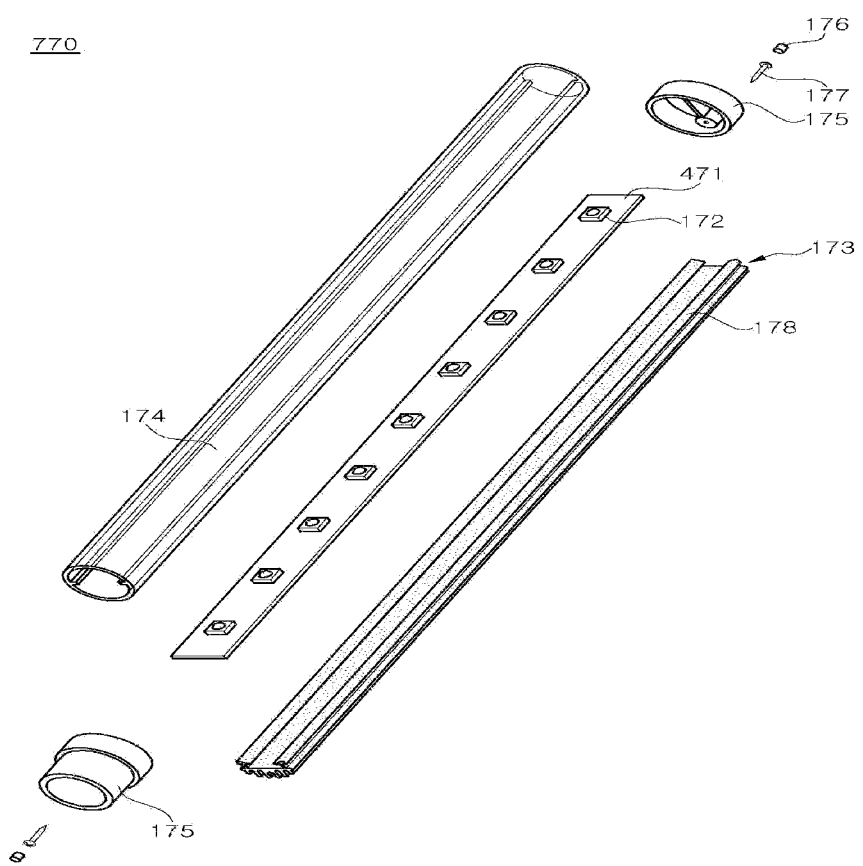
FIG. 17 shows a light source according to an embodiment of the present disclosure.

FIG. 12 through FIG. 17 show various embodiments of light sources 170, 270, 370, 470, 570, 670, 770 mounted on the light source mount 130 of the adhesive-type insect trap 2000, 3000, 4000, 5000, 6000, 7000, 8000 or 9000. FIG. 12 shows a light source having a single support member according to an embodiment of the present disclosure. FIG. 13 shows a light source having a stack of support members according to an embodiment of the present disclosure. FIG. 14 shows a light source having a different arrangement of light emitting diodes from FIG. 13 according to an embodiment of the present disclosure. FIG. 15 shows a light source mounted on a polygonal column-shaped support member according to an embodiment of the present disclosure. FIG. 16 shows a light source mounted on a cylindrical support member according to an embodiment of the present disclosure. FIG. 17 shows a light source according to an embodiment of the present disclosure.

The light source 170, 270, 370, 470, 570, 670 or 770 may include light emitting diodes 172 attached to a support member 171, 271, 371 or 471. As shown in FIG. 12 to FIG. 16, the light source 170, 270, 370, 470, 570, 670 or 770 may include a single support member 171 or a stack of support members 171. On the stack of support members 171, the light emitting diodes 172 are disposed in a zigzag arrangement to suppress damage to the support members by heat therefrom.

Referring to FIG. 15 and FIG. 16, the light source 570 or 670 includes the light emitting diodes 172 mounted on a polygonal column-shaped support member 570 or a cylindrical support member 670 to reduce the volume of the adhesive-type insect trap 2000, 3000, 4000, 5000, 6000, 7000, 8000 or 9000 while allowing emission of light in a broad range, thereby improving light irradiation efficiency. By way of example, a triangular support member 570 may be formed by coupling three PCBs in a triangular shape.

In another embodiment, the support member may include a flexible support member. The flexible support member may be entirely or partially bendable. That is, in order to reduce the size of the adhesive-type insect trap 2000, 3000, 4000, 5000, 6000, 7000, 8000 or 9000 according to the embodiments of the disclosure while improving insect attraction efficiency, the light source mount may have a bent shape or may be bendable and the flexible support member may be mounted on a light source mount (not shown) having a bent shape or on a light source mount (not shown) deformed in a bent shape.

Referring to FIG. 17, the light source 770 may be a tube type LED. The tube type LED 770 may be electrically connected to an external power supply via wire bonding or without wire bonding. By way of example, the tube type LED 770 has a structure in which light emitting diodes 172 are attached to a support member 471 mounted on one surface of a heat sink 173, and includes a case 174 receiving the support member 471 and the heat sink 173 therein and bases 175 coupled to opposite sides of the case 174. By way of example, the heat sink 173 may further include a support member holder 178 surrounding both sides of the support member 471. At least one surface of the support member holder 178 has a gradually increasing height from an inner side thereof, on which the support member 471 is seated, towards an outer periphery thereof. By way of example, the aforementioned support member 171, 271 or 371 may be mounted on the tube type LED 770. By way of example, the tube type LED 770 may include light emitting diodes 172 attached to both sides of the support member 171 or 471, in which light emitting diodes for insect attraction are attached to one side of the support member and UVC light emitting diodes for sterilization and killing of insects are attached to the other side thereof.

Figure 18:
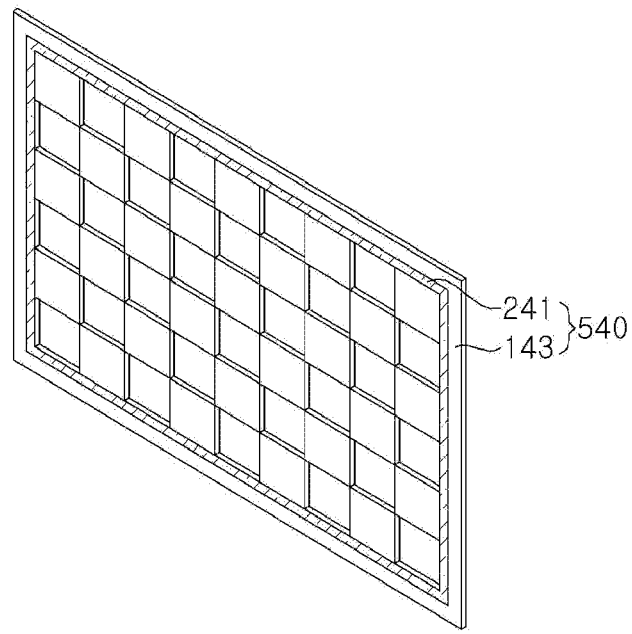
FIG. 18 shows an adhesive sheet including a flypaper piece and a reflective sheet according to embodiments of the present disclosure.

Referring to FIG. 18, in the adhesive-type insect trap 1000, 2000, 3000, 4000, 5000, 6000, 7000, 8000 or 9000, an adhesive sheet 540 includes flypaper pieces 141, 241 and a reflective sheet 143. The reflective sheet 143 may refer to a member on which the flypaper piece 141 or 241 is deposited or coated. Here, the flypaper piece 141 may be formed of a light transmissive material to allow light emitted from the light source to pass therethrough and the flypaper piece 241 may include an opaque material. In this case, the flypaper piece 241 may be disposed in a lattice shape on the reflective sheet 143 such that light emitted from the light source 170 is reflected by the reflective sheet 143 to attract insects. That is, the adhesive-type insect trap 1000, 2000, 3000, 4000, 5000, 6000, 7000, 8000 or 9000 may allow light emitted from the light source 170, 270, 370, 470, 570, 670 or 770 to be reflected by the reflective sheet 143 such that the cover 120 can be irradiated in a large area with the light when the light passes through the cover 120, and may guide insects collected in the adhesive-type insect trap 1000, 2000, 3000, 4000, 5000, 6000, 7000, 8000 or 9000 by the reflected light to remain inside the main body 110, thereby improving insect trapping efficiency. Insects, particularly flies, tend to be more strongly attracted to refracted or diffused light than to direct light. Thus, the adhesive-type insect trap 1000, 2000, 3000, 4000, 5000, 6000, 7000, 8000 or 9000 allow light emitted from the light source 170 to be reflected at least once by the reflective sheet 143 instead of directly passing through the cover, thereby improving insect attraction efficiency with decoy light.

Figure 19:
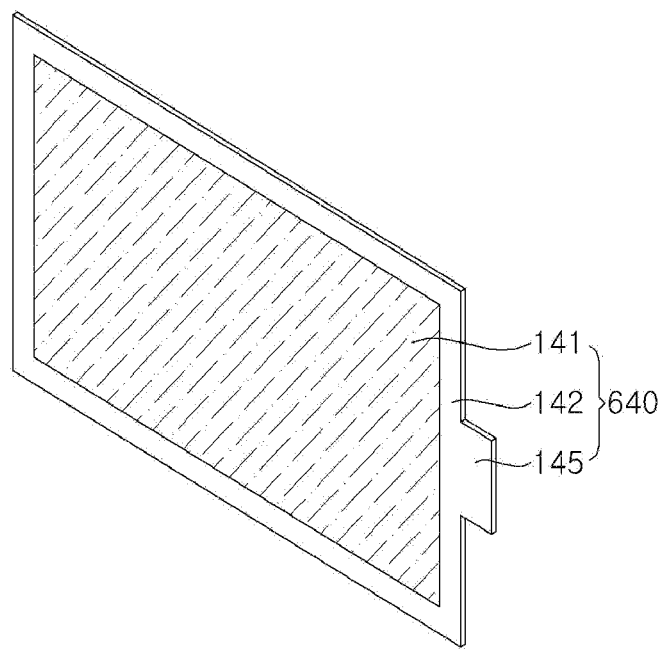
FIG. 19 shows an adhesive sheet including a gripper according to embodiments of the present disclosure.

Referring to FIG. 19, an adhesive sheet 640 includes a gripper 145, which extends a predetermined length therefrom to allow a user to easily grip the gripper 145 upon insertion or separation of the adhesive sheet 640 into or from the adhesive-type insect trap 1000, 2000, 3000, 4000, 5000, 6000, 7000, 8000 or 9000 in a vertical direction or in a horizontal direction. Accordingly, the adhesive sheet 640 may be provided to the adhesive-type insect trap by inserting the adhesive sheet 140 into a space between the main body 110 and the guide groove 111 in a downward direction or in a leftward direction using the gripper 145, and may be replaced by separating the adhesive sheet 640 therefrom in an upward direction or in a rightward direction using the gripper 145.

Figure 20:
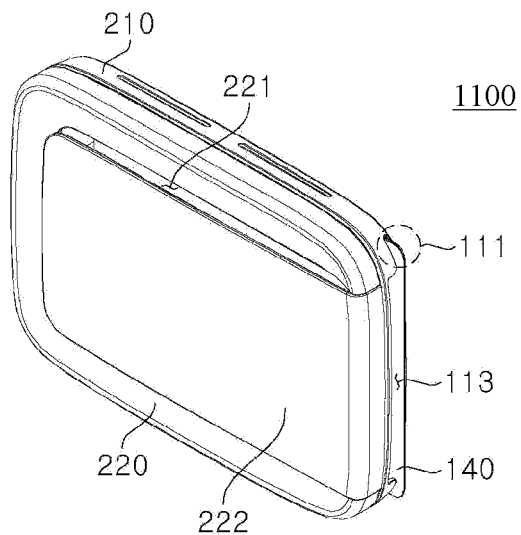
FIG. 20 shows an adhesive-type insect trap having a cover with a through-hole blocking structure according to an embodiment of the present disclosure.
Figure 21:
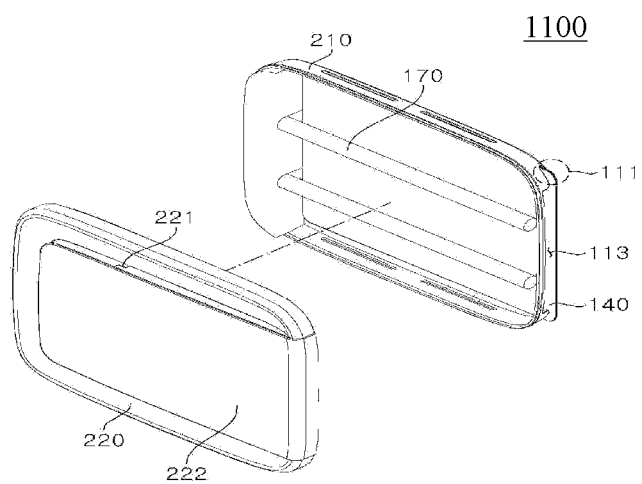
FIG. 21 shows a dissembled state of the adhesive-type insect trap of FIG. 21 according to an embodiment of the present disclosure.
Figure 22:
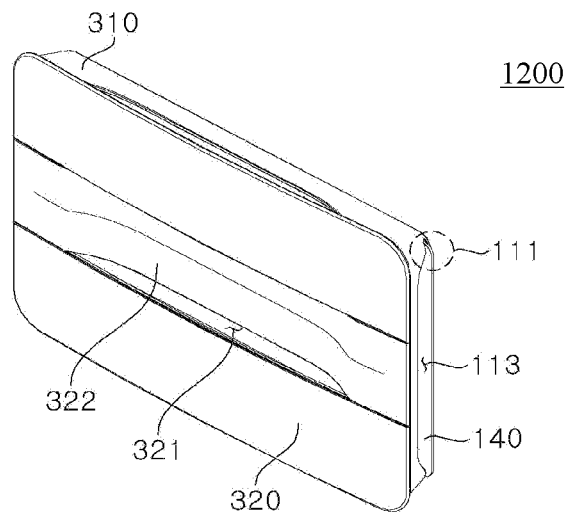
FIG. 22 shows an adhesive-type insect trap showing a cover having a concavely depressed through-hole according to an embodiment of the present disclosure.
Figure 23:
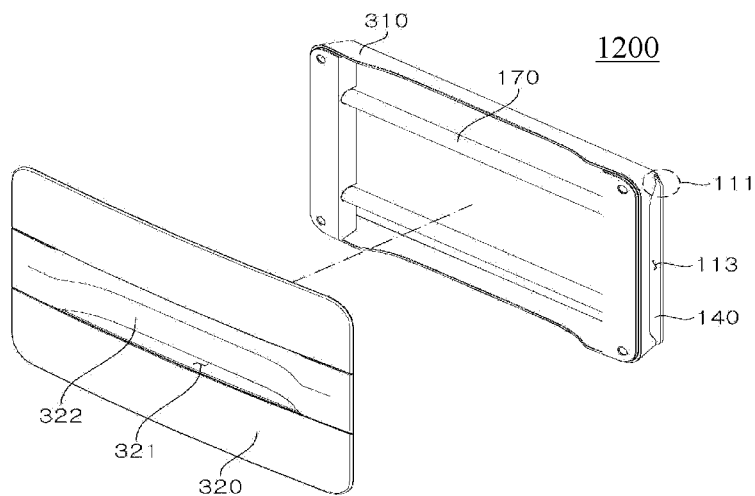
FIG. 23 shows a dissembled state of the adhesive-type insect trap of FIG. 22 according to an embodiment of the present disclosure.

Referring to FIG. 20 to FIG. 23, adhesive-type insect traps 1100, 1200 may adopt the structure of the adhesive-type insect trap 1000, 2000, 3000, 4000, 5000, 6000, 7000, 8000 or 9000, and the following description will focus on various embodiments of covers 220, 320. FIG. 20 shows an adhesive-type insect trap having a cover with a through-hole blocking structure according to an embodiment of the present disclosure. FIG. 21 shows a dissembled state of the adhesive-type insect trap of FIG. 21 according to an embodiment of the present disclosure. FIG. 22 shows an adhesive-type insect trap showing a cover having a concavely depressed through-hole according to an embodiment of the present disclosure. FIG. 23 shows a dissembled state of the adhesive-type insect trap of FIG. 22 according to an embodiment of the present disclosure.

Referring to FIG. 20 and FIG. 21, in the adhesive-type insect trap 1100, the cover 220 may include a through-hole blocking structure 222 adapted to block at least a portion of a through-hole 221, which may be depressed into the cover 220. For example, the through-hole blocking structure 222 may extend from an edge of the cover 220 in a horizontal direction of the cover 220. That is, the adhesive-type insect trap 1100 is configured to maximize the area of the through-hole 221 to improve insect trapping efficiency and to prevent the through-hole blocking structure 222 from protruding from the cover 220 so as to reduce the volume thereof, thereby enabling miniaturization thereof.

Referring to FIG. 22 and FIG. 23, in the adhesive-type insect trap 1200, the cover 320 may include a through-hole blocking structure 322 adapted to block at least a portion of a through-hole 321, which is concavely depressed into the cover 320. For example, the through-hole blocking structure 322 may be integrally formed with the cover 320 and the through-hole 321 may include a step of the cover 320 formed by the concave shape of the through-hole blocking structure 322. That is, in the adhesive-type insect trap 1200, the through-hole blocking structure 322 prevents the adhesive sheet 140 from being viewed through the through-hole 321 from the outside so as to prevent insects attached to the adhesive sheet 140, 240, 340, 440, 540 or 640 from being observed from the outside and does not protrude outwards from the cover 320, thereby enabling miniaturization of the adhesive-type insect trap 1200.

Figure 24:
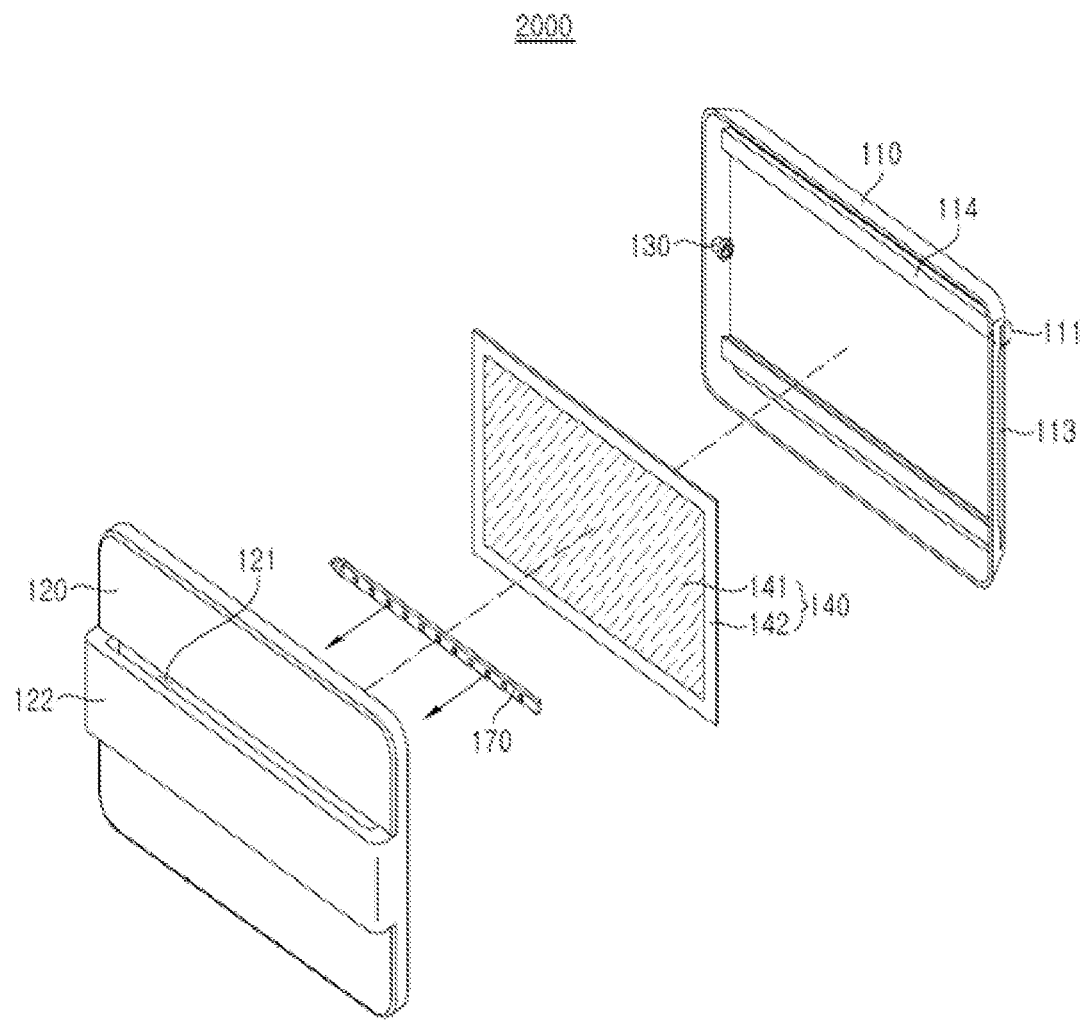
FIG. 24 shows an adhesive-type insect trap having a main body with a guide rail according to an embodiment of the present disclosure.

Referring to FIG. 24, in the adhesive-type insect trap 1000, 2000, 3000, 4000, 5000, 6000, 7000, 8000, 9000, 1100 or 1200, the main body 110 may have a guide rail 114 which guides the adhesive sheet 140, 240, 340, 440, 540 or 640 into the main body 110. The guide rail 114 may guide the adhesive sheet 140, 240, 340, 440, 540 or 640 to be secured inserted into the main body 110 along the guide groove 111 or 211 without being adhered to the main body 110. Further, the guide rail 114 may have a thickness corresponding to a thickness of the adhesive sheet 140, 240, 340, 440, 540 or 640 to allow easy insertion and separation of the adhesive sheet 140, 240, 340, 440, 540 or 640 while receiving an edge of the adhesive sheet 140, 240, 340, 440, 540 or 640 inserted thereinto, and a depth preventing the flypaper piece 141 of the adhesive sheet 140, 240, 340, 440, 540 or 640 from contacting the main body 110.

Figure 25:
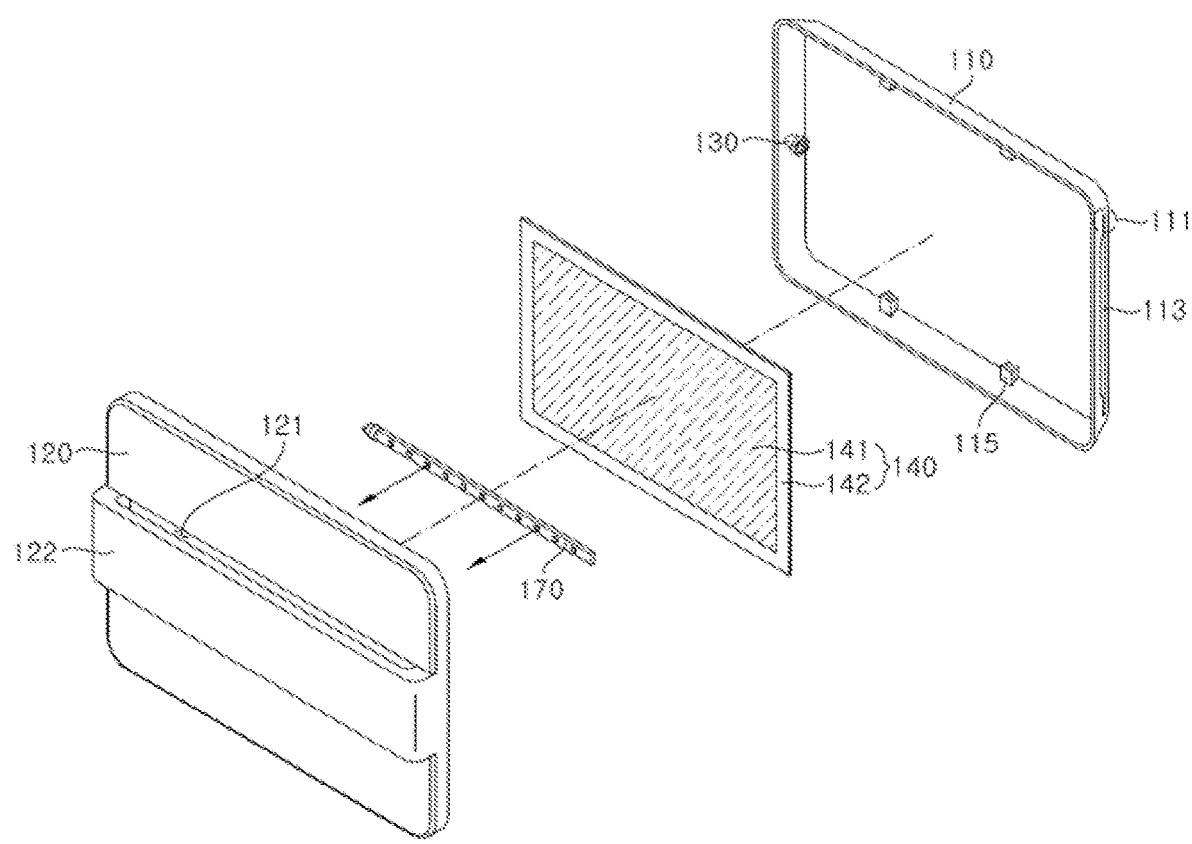
FIG. 25 shows an adhesive-type insect trap having a main body with one exemplary adhesive sheet support according to an embodiment of the present disclosure.
Figure 26:
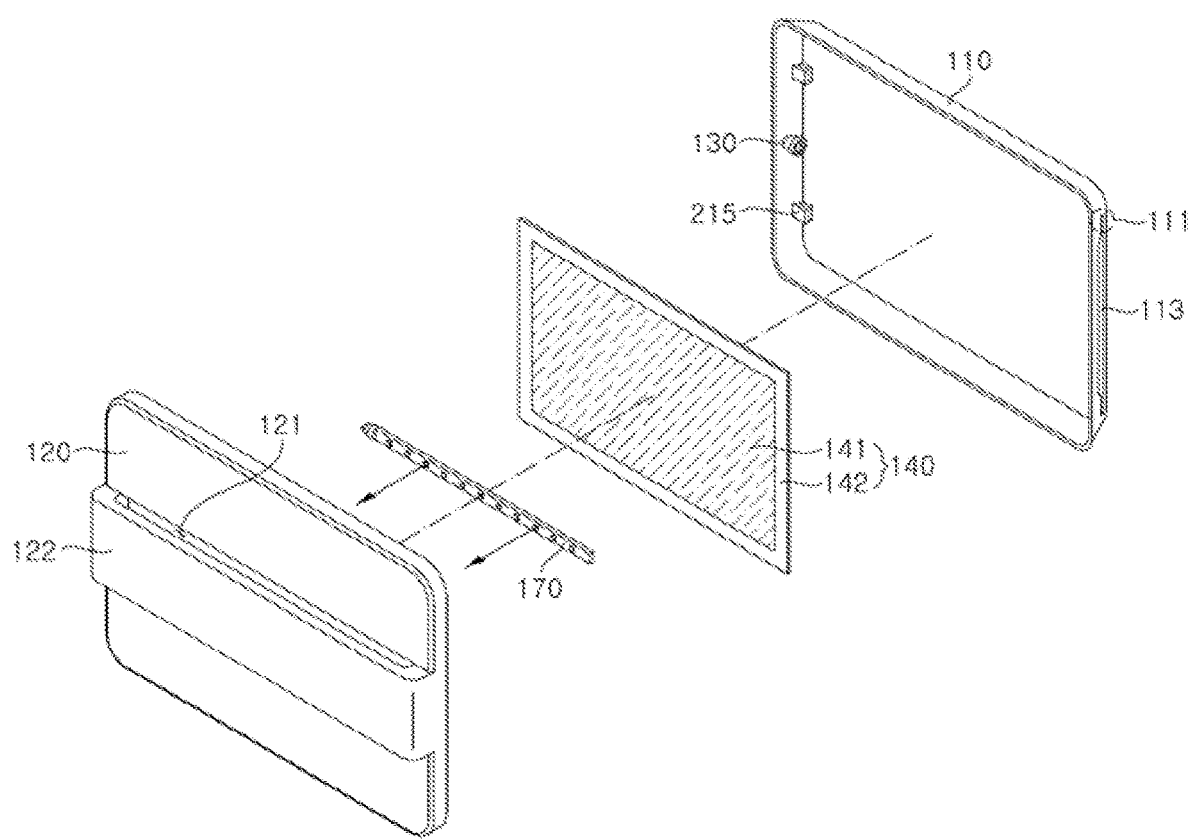
FIG. 26 shows an adhesive-type insect trap having a main body with another exemplary adhesive sheet support according to an embodiment of the present disclosure.

Referring to FIG. 25 and FIG. 26, in the adhesive-type insect trap 1000, 2000, 3000, 4000, 5000, 6000, 7000, 8000, 9000, 1100 or 1200, the main body 110 may include an adhesive sheet support 115 or 215. The adhesive sheet support 115 or 215 may support or secure the adhesive sheet 140, 240, 340, 440, 540 or 640 to prevent the adhesive sheet 140, 240, 340, 440, 540 or 640 inserted into the main body 110 from being adhered to the main body 110.

Figure 27:
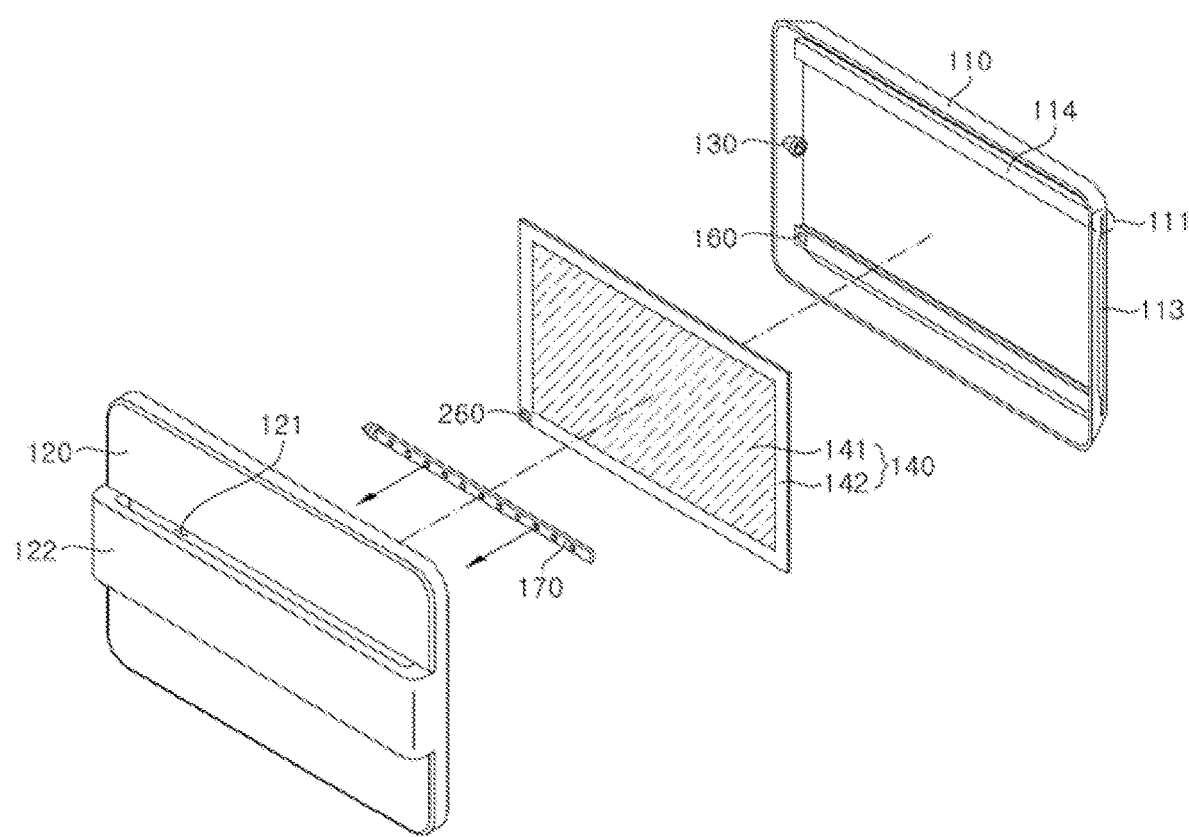
FIG. 27 shows an adhesive-type insect trap having magnet members according to an embodiment of the present disclosure.

Referring to FIG. 27, in the adhesive-type insect trap 1000, 2000, 3000, 4000, 5000, 6000, 7000, 8000, 9000, 1100 or 1200, the guide rail 114 and the adhesive sheet 140, 240, 340, 440, 540 or 640 may include magnet members 160, 260 disposed to face each other and having opposite polarities. That is, the adhesive sheet 140, 240, 340, 440, 540 or 640 are prevented from being separated from the main body even upon rotation of the adhesive-type insect trap 1000, 2000, 3000, 4000, 5000, 6000, 7000, 8000, 9000, 1100 or 1200 according to installation environments by a user after the adhesive sheet 140, 240, 340, 440, 540 or 640 is inserted into the main body 110.

The adhesive-type insect trap 1000, 2000, 3000, 4000, 5000, 6000, 7000, 8000, 9000, 1100 or 1200 may further include a photocatalyst. For example, the photocatalyst may be coated or attached to the rear side of the cover 120, the front side or the lateral side of the main body 110, the reflector 150 or 250, and the adhesive sheet 140, 240, 340 or 440. Alternatively, a separate photocatalyst filter may be mounted on the adhesive-type insect traps.

The photocatalyst may include photocatalyst media generating photocatalytic reaction. For example, the photocatalyst media may include titanium oxide ($TiO_2$), silicon oxide ($SiO_2$), tungsten oxide ($WO_3$), zirconium oxide ($ZnO$), strontium titanium oxide ($SrTiO_3$), niobium oxide ($Nb_2O_5$), iron oxide ($Fe_2O_3$), zinc oxide ($ZnO_2$), tin oxide ($SnO_2$), and the like.

In addition, hydroxyl radicals generated by photocatalytic reaction of the photocatalyst act as a strong oxidant, which performs a sterilization function, and decomposes contaminants and odorous substances in air, which has flown into the adhesive-type insect trap 1000, 2000, 3000, 4000, 5000, 6000, 7000, 8000, 9000, 1100 or 1200, into water and carbon dioxide by decomposing organic contaminants in air through oxidation. Here, carbon dioxide is known as a substance having an effect of attracting mosquitoes.

As such, the adhesive-type insect trap 1000, 2000, 3000, 4000, 5000, 6000, 7000, 8000, 9000, 1100 or 1200 further include the photocatalyst to provide not only sterilization and deodorization effects, but also an effect of attracting insects, particularly mosquitoes, through generation of carbon dioxide during photocatalytic reaction.

The adhesive-type insect trap 1000, 2000, 3000, 4000, 5000, 6000, 7000, 8000, 9000, 1100 or 1200 may further include a switch (not shown) for controlling a power supply system of the light source mount 130. Here, a power supply may be disposed at any location without being limited to a particular location.

In addition, the adhesive-type insect trap 1000, 2000, 3000, 4000, 5000, 6000, 7000, 8000, 9000, 1100 or 1200 may include a camera to allow a user to observe insects trapped on the adhesive sheet 140, 240, 340 or 440. The camera may have a zoom function, whereby a user can move the camera or use the zoom function at a remote location through transmission of a signal to a communication module mounted on the adhesive-type insect trap 1000, 2000, 3000, 4000, 5000, 6000, 7000, 8000, 9000, 1100 or 1200 when photographing insects trapped in the adhesive-type insect trap 1000, 2000, 3000, 4000, 5000, 6000, 7000, 8000, 9000, 1100 or 1200.

Further, the adhesive-type insect trap 1000, 2000, 3000, 4000, 5000, 6000, 7000, 8000, 9000, 1100 or 1200 may include a sensor to allow a user to ascertain the presence of insects trapped in the insect trap or to ascertain an area of the adhesive sheet 140, 240, 340 or 440 occupied by insects trapped thereon, and may perform a notification function to a user through the communication module when the sensor detects that insects are trapped or that the area of the adhesive sheet occupied by insects trapped thereon exceeds a preset value. By way of example, the sensor may include a brightness sensor for detecting brightness of the adhesive sheet 140, 240, 340 or 440. The brightness sensor may detect a collected amount of insects through brightness comparison between a region to which insects are attached and a region to which no insects are attached.

Further, the adhesive-type insect trap 1000, 2000, 3000, 4000, 5000, 6000, 7000, 8000, 9000, 1100 or 1200 may include an insect attractant spray (not shown) or may include an insect attractant contained in an adhesive sheet to improve insect attraction efficiency.

Further, the adhesive-type insect trap 1000, 2000, 3000, 4000, 5000, 6000, 7000, 8000, 9000, 1100 or 1200 may include a light diffusion material applied to or coated on the adhesive sheet 140, 240, 340 or 440 to diffuse light emitted from the light source 170, 270, 370, 470, 570, 670 or 770, thereby improving efficiency in attraction of insects, particularly flies.

Insects, particularly flies, tend to be more strongly attracted to refracted or diffused light than to direct light. The adhesive-type insect trap 1000, 2000, 3000, 4000, 5000, 6000, 7000, 8000, 9000, 1100 or 1200 can refract or diffuse light from the light source 170, 270, 370, 470, 570, 670 or 770, thereby improving efficiency in attraction of insects with decoy light. By way of example, the cover 120, 220 or 320 may have a roughened surface, may include a separate diffusion film attached thereto or coated thereon, or may include a diffusion agent applied thereto or coated thereon, wherein the surface of the cover 120, 220 or 320 includes outer and inner surfaces of the cover 120, 220 or 320. Alternatively, the reflector 150 or 250 may have a roughened surface, may include a separate diffusion film attached thereto or coated thereon, or may include a diffusion agent applied thereto or coated thereon. Alternatively, the light source 170, 270, 370, 470, 570, 670 or 770 may have a roughened surface, may include a separate diffusion film attached thereto or coated thereon, or may include a diffusion agent applied thereto or coated thereon. For example, the case 174 of the light source 770 shown in FIG. 17 may have a roughened surface, may include a separate diffusion film attached thereto or coated thereon, or may include a diffusion agent applied thereto or coated thereon.

Referring to FIG. 28 to FIG. 32, adhesive-type insect traps described below has a structure to allow the adhesive sheet 140, 240, 340, 440, 540 or 640 of the adhesive-type insect trap 1000, 2000, 3000, 4000, 5000, 6000, 7000, 8000, 9000, 1100 or 1200 to be stably inserted thereinto or secured thereto. In a typical insect trap configured to collect insects, such as flies, through adhesion of the insects, chemical reaction of a resin contained in an adhesive sheet thereof occurs due to heat generated from an attraction light source, thereby causing deformation of the adhesive sheet. As a result, an adhesive surface of the adhesive sheet is adhered to the light source or the main body, or is separated from the main body, thereby causing deterioration in collection of insects, such as flies. Accordingly, the inventors of the present disclosure have performed numerous experiments to develop a structure for preventing the adhesive surface of the adhesive sheet 140, 240, 340, 440, 540 or 640 from being adhered to the main body 410 or the light source and invented the structure described hereinafter.

Figure 28:
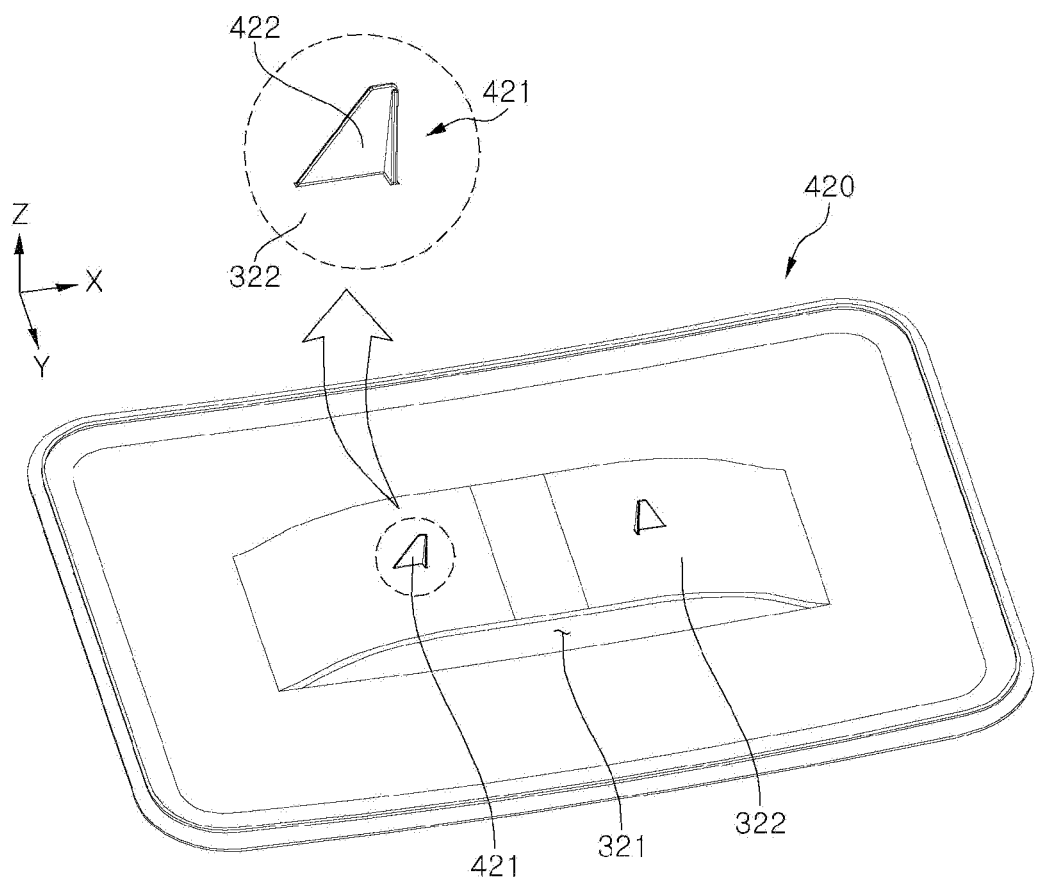
FIG. 28 shows a rear surface of a cover according to one embodiment of the present disclosure.
Figure 29:
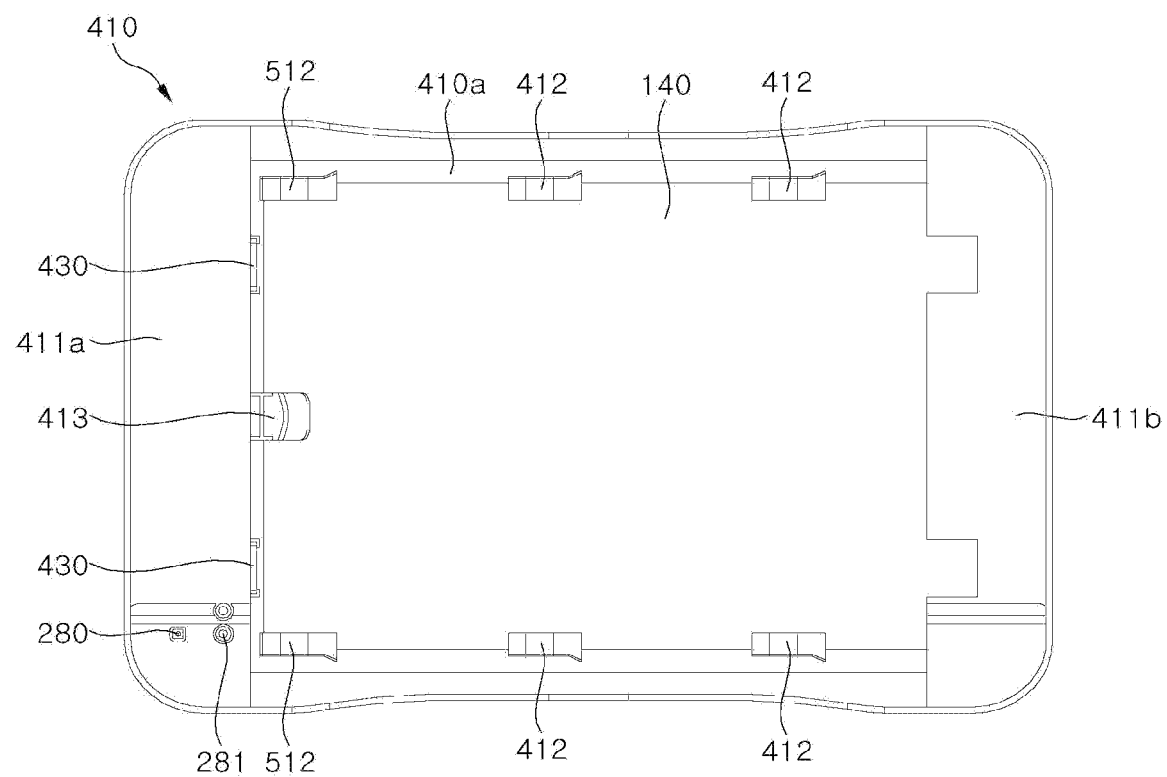
FIG. 29 shows a main body of an adhesive-type insect trap according to one embodiment of the present disclosure, with a cover separated therefrom.
Figure 31:
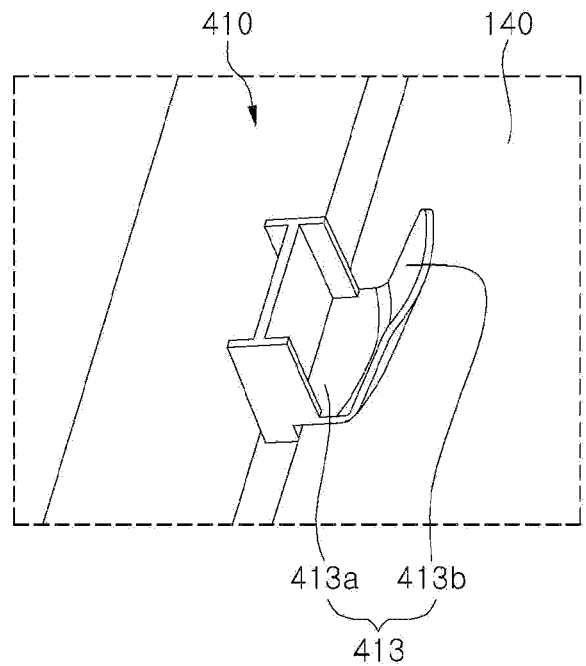
FIG. 31 shows a stopper unit according to one embodiment of the present disclosure.
Figure 32:
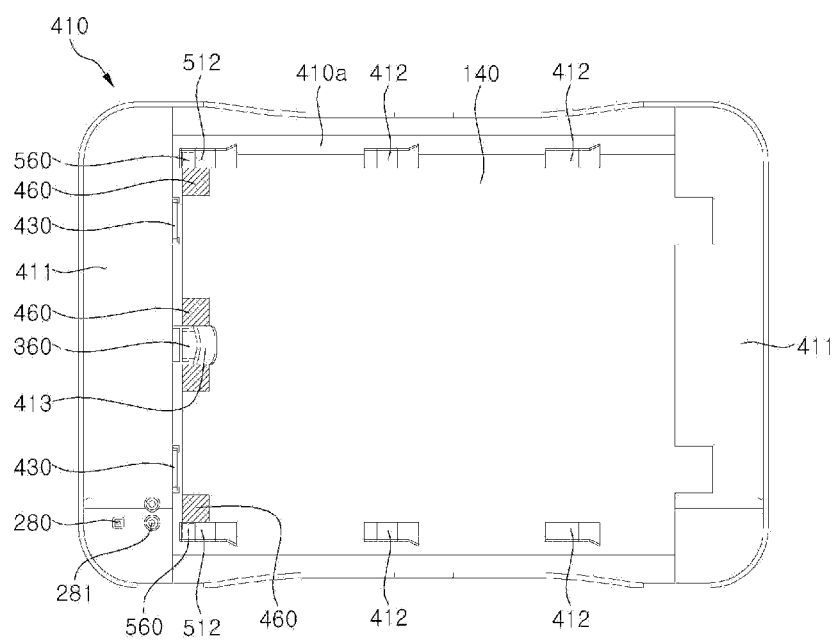
FIG. 32 shows a main body of an adhesive-type insect trap according to one embodiment of the present disclosure, with a cover separated therefrom.

FIG. 28 shows a rear surface of a cover according to one embodiment of the present disclosure. FIG. 29 shows a main body of an adhesive-type insect trap according to one embodiment of the present disclosure, with a cover separated therefrom. FIG. 30 shows a guide member according to one embodiment of the present disclosure, where FIG. 30(*a*) shows one exemplary structure of the guide member, FIG. 30(*b*) shows a cross sectional view of the guide member of FIG. 30(*a*), FIG. 30(*c*) shows another exemplary structure of the guide member, and FIG. 30(*d*) shows a cross sectional view of the guide member of FIG. 30(*c*). FIG. 31 shows a stopper unit according to one embodiment of the present disclosure. FIG. 32 shows a main body of an adhesive-type insect trap according to one embodiment of the present disclosure, with a cover separated therefrom. FIGS. 28-32 will be described more in detail below.

FIG. 28 shows a rear surface of a cover according to one embodiment of the present disclosure. Referring to FIG. 28, the cover 420 may include at least one cover protrusion 421 protruding in a direction in which the corresponding adhesive sheet 140, 240, 340, 440, 540 or 640 is disposed. The cover protrusion 421 is formed on a rear surface of cover to prevent the adhesive sheet 140, 240, 340, 440, 540 or 640 from being excessively bent even when the adhesive sheet 140, 240, 340, 440, 540 or 640 is bent due to the weight thereof or flies attached thereto, or due to heat generated from the light source 170, 270, 370, 470, 570, 670 or 770. For example, the cover protrusion 421 may have a predetermined height in a direction from the cover 420 to a main body bottom 410*a* (see FIG. 29) of the main body to prevent the adhesive sheet 140, 240, 340, 440, 540 or 640 from contacting the light source 170, 270, 370, 470, 570, 670 or 770 even when the adhesive sheet 140, 240, 340, 440, 540 or 640 is bent. That is, the adhesive-type insect trap includes the cover protrusion 421 to prevent the adhesive sheet 140, 240, 340, 440, 540 or 640 from being attached to the main body 410 or the light source 170, 270, 370, 470, 570, 670 or 770, thereby improving efficiency in trapping insects such as flies and the like.

The cover protrusion 421 may be disposed on a concave portion of the cover 420, for example, on the through-hole blocking structure 322 concavely formed on the cover 420. That is, the cover protrusion 421 is formed to have a minimized height while preventing the adhesive sheet 140, 240, 340, 440, 540 or 640 from being attached to the main body 410 or the light source 170, 270, 370, 470, 570, 670 or 770 so as not to obstruct introduction of insects including flies into the main body 410 from being obstructed, thereby improving efficiency in trapping insects such as flies and the like.

The cover protrusion 421 may include a section having an area gradually decreasing in a direction from the cover 420 to the main body bottom 410*a* and a region of the cover protrusion 421 having the smallest cross-sectional area may be disposed at a distal end 422 of the cover protrusion 421 closer to the main body bottom 410*a* than the cover 420. The cross-sectional area of the cover protrusion 421 refers to an area taken in an x-y plane in FIG. 28. When a contact surface between the adhesive sheet 140, 240, 340, 440, 540 or 640 and the cover protrusion 421 has a larger area, the adhesive sheet 140, 240, 340, 440, 540 or 640 can be adhered to the cover protrusion 421. As a result, upon replacement of the adhesive sheet 140, 240, 340, 440, 540 or 640, excessive force is applied to the adhesive sheet 140, 240, 340, 440, 540 or 640 to shake the main body 410, thereby causing deterioration in durability of each component, for example, the light source 170, 270, 370, 470, 570, 670 or 770, a sensor 280, circuits, and the like, in the main body 410, or detachment of insects such as files from the main body. Accordingly, the adhesive-type insect trap minimizes the cross-sectional area of the cover protrusion 421 contacting the adhesive sheet 140, 240, 340, 440, 540 or 640, thereby improving durability of the components in the main body 410 and efficiency in trapping insects including flies.

FIG. 29 shows the main body 410 of the adhesive-type insect trap according to one embodiment of the present disclosure, from which the cover is separated, FIGS. 30(a) through 30(d) show a guide member of the adhesive-type insect trap according to one embodiments of the present disclosure, and FIG. 31 shows a stopper unit of the adhesive-type insect trap according to one embodiment of the present disclosure.

Referring to FIG. 29, the main body 410 of the adhesive-type insect trap includes a main body bottom 410a, side portions 411a, 411b, an adhesive sheet 140, 240, 340, 440, 540 or 640, a guide member 412, and a stopper unit 413.

The main body bottom 410a refers to a region in which the adhesive sheet 140, 240, 340, 440, 540 or 640 is inserted into the main body and disposed at an upper side thereof, the side portions 411a, 411b are disposed at both sides thereof, and the guide member 412 and the stopper unit 413 are disposed. The side portions 411a, 411b may contact the side surfaces of the main body 410 or may be separated a predetermined distance from the main body 410. For example, the side portions may be disposed to contact the side surfaces of the main body 410 to allow efficient use of a space defined in the main body 410. The side portions 411a, 411b may be provided with circuits (not shown) and a power supply (not shown), which supplies power to the light source 170, 270, 370, 470, 570, 670 or 770, the sensor 280, a display unit 281, and the like, and may include a separate housing to prevent damage to the power supply and the circuit due to intrusion of insects or dust. Here, at least a portion of a light source mount 430 may be connected to the side portions 411a. For example, the light source mount 430 may be disposed outside the side portions 411a or inside the side portion 411. The side portions 411a may be further provided with the sensor 280 and the display unit 281. Here, the sensor 280 may include a sensor 290 for detecting, for example, at least one of the kind of insect trapped on the adhesive sheet 140, 240, 340, 440, 540 or 640, an area of the adhesive sheet 140, 240, 340, 440, 540 or 640 trapping insects, brightness of the adhesive sheet 140, 240, 340, 440, 540 or 640, an ambient temperature of the light source 170, the intensity of light emitted from the light source 170, illuminance of ambient light around the adhesive-type insect trap, insertion of the adhesive sheet 140, 240, 340, 440, 540 or 640 into the insect trap, and attachment of the cover 120 to the insect trap, as described above.

For example, the sensor 280 may include a UV sensor, an illuminance sensor, a temperature sensor, a magnetic sensor, a limit sensor, a photosensor, and the like. The display unit 281 may emit indication light when data values detected by the sensor 280 are greater than or less than preset values. For example, when the intensity of light emitted from the light source 170, 270, 370, 470, 570, 670 or 770 detected by the UV sensor is less than a preset range, the display unit 281 may emit indication light, which may indicate a light source replacement signal. For example, when the ambient temperature around the light source 170, 270, 370, 470, 570, 670 or 770 detected by the temperature sensor exceeds a preset range, the display unit 281 may emit indication light, which may indicate a warning signal of the light source 170, 270, 370, 470, 570, 670 or 770. For example, when no insertion of the adhesive sheet 140, 240, 340, 440, 540 or 640 or incomplete attachment of the cover 120, 220 or 320 is detected by the magnetic sensor or the limit sensor, the display unit 281 may emit indication light, which may indicate a signal indicating incomplete preparation for operation. The side portion 411 may be provided in plural. For example, the side portion 411b is disposed on a side surface of the main body 410 corresponding to the side portion 411a inside the main body 410 to prevent the weight of the main body from being concentrated in a direction in which the side portion 411a is disposed, thereby further improving efficiency in trapping flies through stable installation of the insect trap.

The guide member 412 guides the adhesive sheet 140, 240, 340, 440, 540 or 640 to be stably inserted into the main body 410 and may be provided in plural. For example, the guide members 412 may be separated from each other by a predetermined distance. By way of example, at least two guide members 412 may be disposed on opposite surfaces with reference to the adhesive sheet 140, 240, 340, 440, 540 or 640. For example, three guide members 412 may be disposed on each of the opposite surfaces with reference to the adhesive sheet 140, 240, 340, 440, 540 or 640. Here, the guide members 412 disposed at locations at which the adhesive sheet 140, 240, 340, 440, 540 or 640 reaches the deepest depth may include a wall having a predetermined height to stop movement of the adhesive sheet 140, 240, 340, 440, 540 or 640. That is, the adhesive-type insect trap allows the adhesive sheet 140, 240, 340, 440, 540 or 640 to be inserted along the plural guide members 412 separated from each other by a predetermined distance, instead of being inserted along the guide rails extending in an insertion direction of the adhesive sheet 140, 240, 340, 440, 540 or 640, thereby preventing difficulty in insertion and separation of the adhesive sheet 140, 240, 340, 440, 540 or 640 due to attachment of the adhesive sheet 140, 240, 340, 440, 540 or 640 to the guide rails, or further improving efficiency in trapping flies by securing a larger area for trapping flies.

Referring to FIG. 30(a) through 30(d), the guide member 412 may include at least two plates 412a, 412b and a slanted portion 412c. The at least two plates 412a, 412b may have different heights from the main body bottom 410a.

Figure 30A:
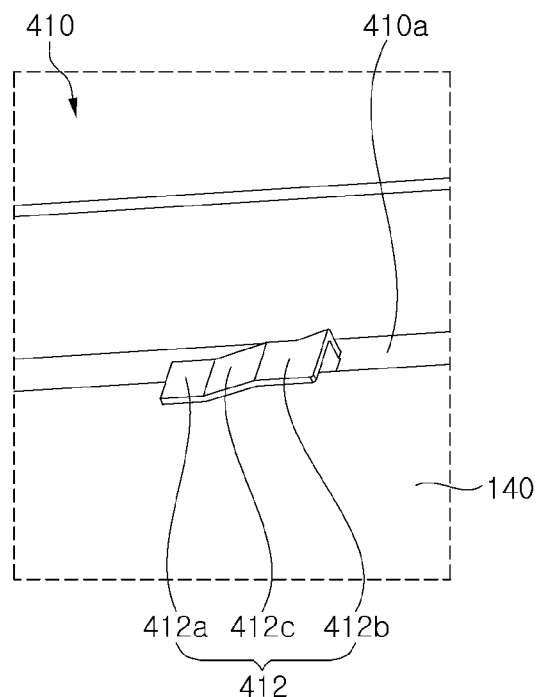
FIG. 30(a) shows one exemplary structure of the guide member.
Figure 30B:
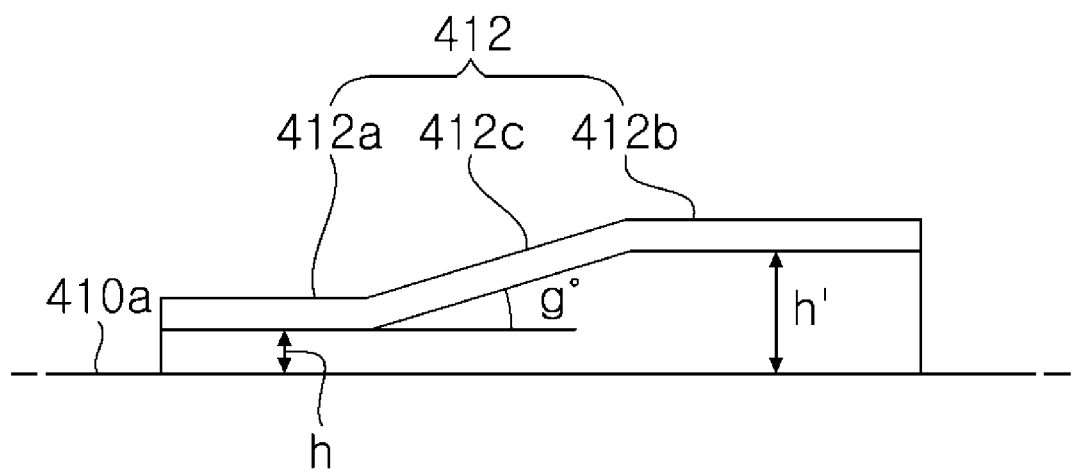
FIG. 30(b) shows a cross sectional view of the guide member of FIG. 30(a)

Referring to FIG. 30(a) and FIG. 30(b), the plate 412c disposed near the adhesive sheet insertion hole 113 may have a greater height h' from the main body bottom 410a than the plate 412a disposed apart from the adhesive sheet insertion hole 113 and having a height h from the main body bottom 410a. In addition, the slanted portion 412c may be disposed between the plates 412a, 412b. The slanted portion 412c may have a larger inclination (g) than an angle (approaching 0° in FIG. 30(b)) defined between the plate 412a having the lowest height in one guide member 412 and the main body bottom 410a. That is, the adhesive sheet 140, 240, 340, 440, 540 or 640 inserted into the main body 410 can easily pass through the plate 412b having a greater height from the main body bottom 410a and then can smoothly pass through the plate 412a having a lower height along the slanted portion 412c. Accordingly, in the adhesive-type insect trap, the guide member 412 includes at least two plates 412a, 412b having different heights and the slanted portion 412c to allow easy insertion of the adhesive sheet 140, 240, 340, 440, 540 or 640, thereby preventing the adhesive sheet 140, 240, 340, 440, 540 or 640 from being bent or unstably inserted into the main body 410 upon insertion of the adhesive sheet 140, 240, 340, 440, 540 or 640 into the main body to improve efficiency in trapping insects such as flies and the like.

Figure 30C:
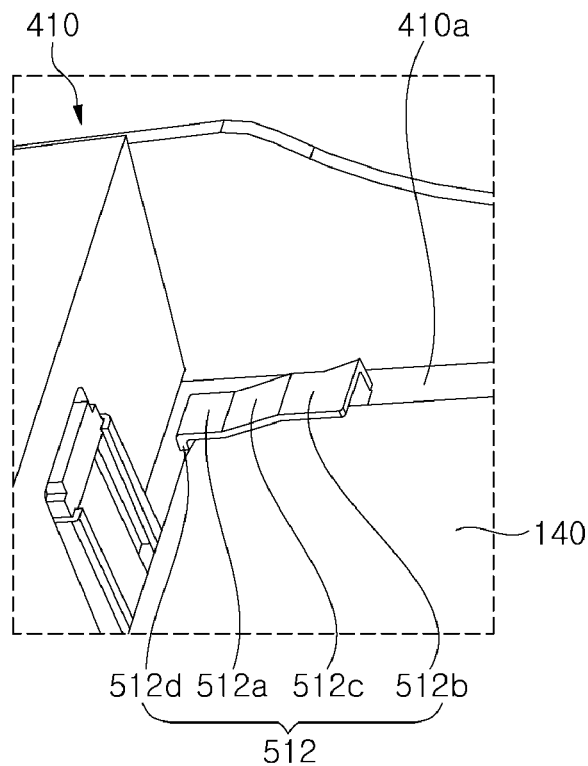
FIG. 30(c) shows another exemplary structure of the guide member.
Figure 30D:
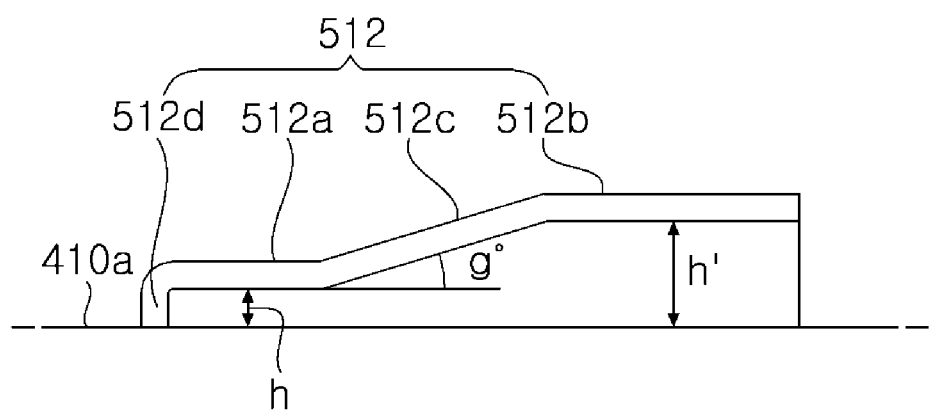
FIG. 30(d) shows a cross sectional view of the guide member of FIG. 30(c).

Referring to FIG. 30(c) and FIG. 30(d), a guide member 512 may further include an end wall 512d unlike the guide member 412. The guide member 512 may be disposed at a portion at which the adhesive sheet 140, 240, 340, 440, 540 or 640 reaches the deepest location on the main body bottom 410a, in order to stop insertion of the adhesive sheet 140, 240, 340, 440, 540 or 640. The end wall 512d may be disposed in a width direction (d) of the plates 412a, 412b to stop movement of the adhesive sheet 140, 240, 340, 440, 540 or 640 and may extend from the main body bottom 410a. That is, the adhesive-type insect trap allows the adhesive sheet 140, 240, 340, 440, 540 or 640 to be inserted along the plural guide members 412, 512 separated from each other by a predetermined distance, instead of being inserted along the guide rails extending in the insertion direction of the adhesive sheet 140, 240, 340, 440, 540 or 640, thereby preventing difficulty in insertion and separation of the adhesive sheet 140, 240, 340, 440, 540 or 640 due to attachment of the adhesive sheet 140, 240, 340, 440, 540 or 640 to the guide rail, or further improving efficiency in trapping flies by securing a larger area for trapping flies.

Referring to FIG. 31, the stopper unit 413 allows the adhesive sheet 140, 240, 340, 440, 540 or 640 to be stably inserted into the main body 410 and secured thereto, and may be provided singularly or in plural. For example, the stopper unit may be disposed between the plural light source mounts 430. The stopper unit 413 may include a stopper plate 413a and a tongue portion 413b. The stopper plate 413a may be substantially parallel to the main body bottom 410a and allows the adhesive sheet 140, 240, 340, 440, 540 or 640 to be inserted into and secured in a space defined between the stopper plate 413a and the main body bottom 410a. The tongue portion 413b is slanted in a direction in which the adhesive sheet insertion hole 113 is disposed, and serves to allow a distal end of the adhesive sheet 140, 240, 340, 440, 540 or 640 to be smoothly inserted into the space between the stopper plate 413a and the main body bottom 410a along the tongue portion 413b. For example, the tongue portion 413b has a round shape, for example, a substantially U shape, which convexly protrudes towards the adhesive sheet insertion hole 113, and serves to guide the distal end of the adhesive sheet 140, 240, 340, 440, 540 or 640 to be smoothly inserted into the space between the stopper plate 413a and the main body bottom 410a along the tongue portion 413b when inserted into the main body 410. When the stopper plate 413a is composed of a resilient piece, the stopper plate 413a may be disposed to adjoin the main body bottom 410a. For example, a user may secure the adhesive sheet 140, 240, 340, 440, 540 or 640 to the stopper unit 413 by applying force to the tongue portion 413b in an insertion direction of the adhesive sheet 140, 240, 340, 440, 540 or 640 to form a space between the stopper plate 413a and the main body bottom 410a, and inserting the adhesive sheet 140, 240, 340, 440, 540, 640 into the space, followed by releasing the force applied to the tongue portion 413b. As such, the adhesive-type insect trap includes the stopper unit 413 to secure the adhesive sheet 140, 240, 340, 440, 540 or 640 to the stopper unit 413, in which the tongue portion 413b of the stopper unit 413 is slanted in a predetermined direction to allow the adhesive sheet 140, 240, 340, 440, 540 or 640 to be smoothly inserted into and secured to the main body without being bent, whereby the adhesive sheet 140, 240, 340, 440, 540 or 640 adapted to directly trap flies and the like can be stably secured in the insect trap, thereby improving efficiency in trapping flies and the like.

FIG. 32 shows an adhesive-type insect trap according to one embodiment of the present disclosure, with a cover separated from a main body thereof. Referring to FIG. 32, the adhesive-type insect trap may include the components of the adhesive-type insect traps described with reference to FIG. 28 to FIG. 31 except for magnet members 360, 460, 560 having opposite polarities and disposed at locations at which the guide member 412 or the stopper unit 413 faces the adhesive sheet 140, 240, 340, 440, 540 or 640. For example, the guide member 412 may include magnet members 560 at lower ends of the plates 412a, 412b substantially parallel to the main body bottom 410a, and the stopper unit 413 may include magnet members 360 at lower ends of the stopper plate 413a substantially parallel to the main body bottom 410a. For example, the magnet members 560 are provided to the guide members 412 disposed at the locations at which the adhesive sheet 140, 240, 340, 440, 540 or 640 reaches the deepest depth, among the plural guide members 412, thereby allowing the adhesive sheet 140, 240, 340, 440, 540 or 640 to be stably inserted into the main body 410 without any obstruction. As such, the adhesive-type insect trap further includes the magnet members 360, 460, 560 to allow the adhesive sheet 140, 240, 340, 440, 540 or 640 adapted to directly collect flies and the like to be stably secured in the insect trap, thereby improving efficiency in trapping flies and the like.

Adhesive-type insect traps described below with reference to FIG. 33 to FIG. 37 further include a feature allowing a plurality of adhesive sheets 140, 240, 340, 440, 540, 640 to be stably inserted into and secured thereto or a feature allowing easy replacement of the adhesive sheet 140, 240, 340, 440, 540 or 640 using a plurality of flypaper pieces 141, 241 included in a single adhesive sheet 140, 240, 340, 440, 540 or 640, in addition to the structures of the adhesive-type insect traps 1000, 2000, 3000, 4000, 5000, 6000, 7000, 8000, 9000, 1100, 1200. In a typical insect trap including an adhesive sheet to collect insects, the adhesive sheet is not stably disposed therein and thus can be partially separated or bent due to physical impact of insects, thereby causing deterioration in insect trapping efficiency. Further, since the typical insect trap employs only a single adhesive sheet, the typical insect trap provides user inconvenience in insertion and separation of the adhesive sheet and can generate physical impact, such as shaking and the like, during insertion and separation of the adhesive sheet, thereby causing detachment of insects from the adhesive sheet or deterioration in durability of each component therein. Accordingly, the inventors of the present disclosure have performed numerous experiments to develop a structure enabling stable installation of the adhesive sheets within the main body, wherein a plurality of adhesive sheets is inserted into the main body or a single adhesive sheet includes a plurality of flypaper pieces, thereby improving insect trapping efficiency and durability of each component thereof.

Figure 33:
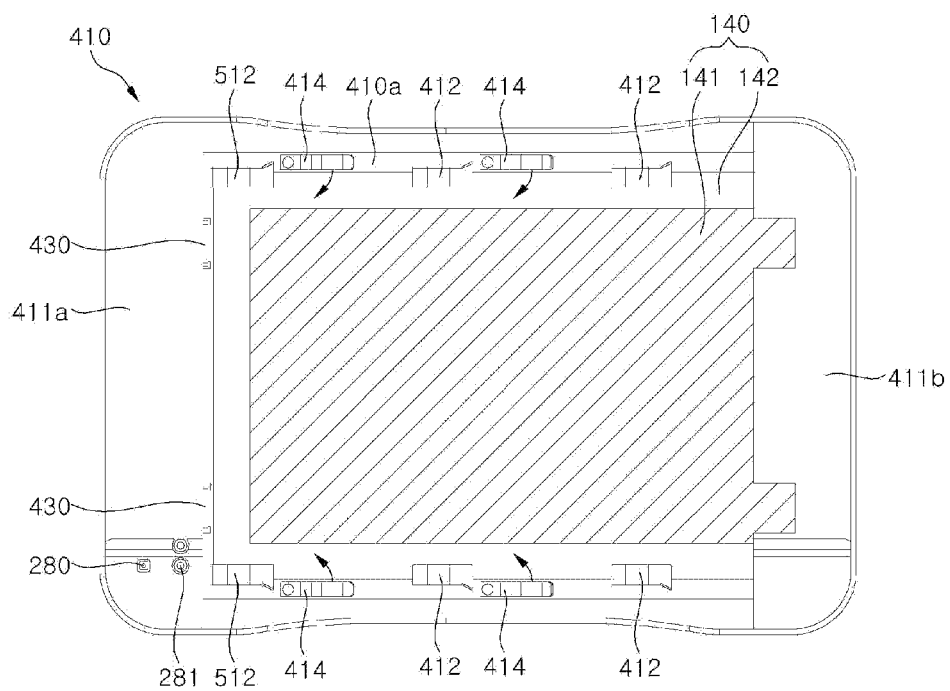
FIG. 33 shows a main body of an adhesive-type insect trap according to one embodiment of the present disclosure, with a cover separated therefrom.
Figure 34:
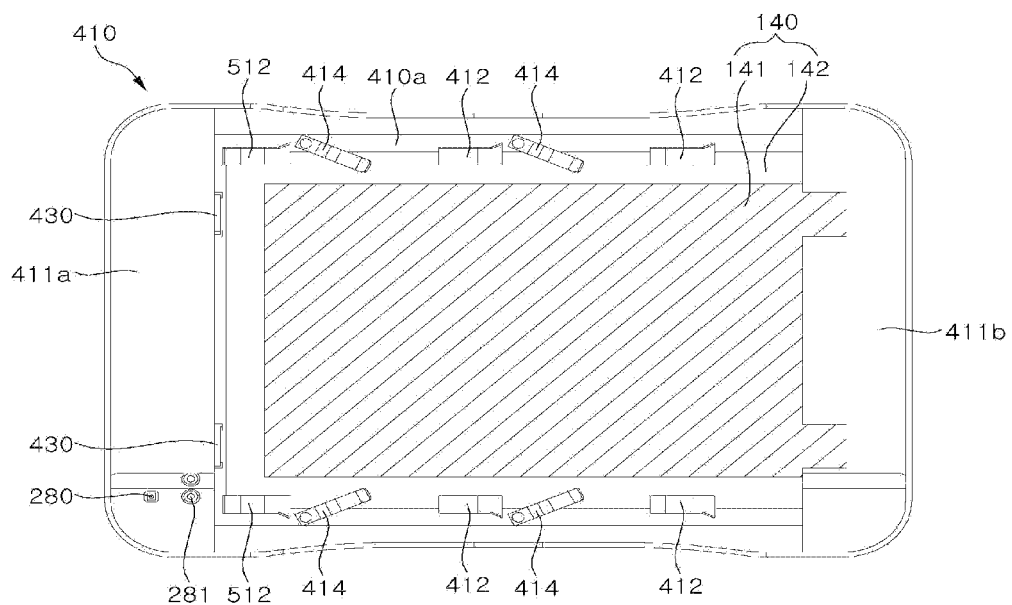
FIG. 34 shows that a securing member secures an adhesive sheet in the main body shown in FIG. 33.

FIG. 33 and FIG. 34 show an adhesive-type insect trap according to one embodiment of the present disclosure, with a cover separated therefrom Referring to FIG. 33 and FIG. 34, the main body 410 of the adhesive-type insect trap includes a main body bottom 410a, side portions 411a, 411b, an adhesive sheet 140, 240, 340, 440, 540 or 640, a securing member 413, and a guide member 412.

The main body bottom 410a refers to a region in which the adhesive sheet 140, 240, 340, 440, 540 or 640 is inserted into the main body and disposed at an upper side thereof, the side portions 411a, 411b are disposed at both sides thereof, and the guide member 412 and the securing member 413 are disposed. The side portions 411a, 411b may contact the side surfaces of the main body 410 or may be separated a predetermined distance from the main body 410. For example, the side portions may be disposed to contact the side surfaces of the main body 410 to allow efficient use of a space defined in the main body 410. The side portions 411a, 411b may be provided with circuits (not shown) and a power supply (not shown), which supplies power to the light source 170, 270, 370, 470, 570, 670 or 770, the sensor 280, the display unit 281, and the like, and may include a separate housing to prevent damage to the power supply and the circuit due to intrusion of insects or dust. Here, at least a portion of the light source mount 430 may be connected to the side portion 411a. For example, the light source mount 430 may be disposed outside the side portions 411a or inside the side portion 411. The side portions 411a may be further provided with the sensor 280 and the display unit 281. Here, the sensor 280 may include a sensor 290 for detecting, for example, at least one of the kind of insect trapped on the adhesive sheet 140, 240, 340, 440, 540 or 640, an area of the adhesive sheet 140, 240, 340, 440, 540 or 640 trapping insects, brightness of the adhesive sheet 140, 240, 340, 440, 540 or 640, an ambient temperature of the light source 170, the intensity of light emitted from the light source 170, illuminance of ambient light around the adhesive-type insect trap, insertion of the adhesive sheet 140, 240, 340, 440, 540 or 640 into the insect trap, and attachment of the cover 120 to the insect trap, as described above.

For example, the sensor 280 may include a UV sensor, an illuminance sensor, a temperature sensor, a magnetic sensor, a limit sensor, a photosensor, and the like. The display unit 281 may emit indication light when data values detected by the sensor 280 are greater than or less than preset values. For example, when the intensity of light emitted from the light source 170, 270, 370, 470, 570, 670 or 770 detected by the UV sensor is less than a preset range, the display unit 281 may emit indication light, which may indicate a light source replacement signal. For example, when the ambient temperature around the light source 170, 270, 370, 470, 570, 670 or 770 detected by the temperature sensor exceeds a preset range, the display unit 281 may emit indication light, which may indicate a warning signal of the light source 170, 270, 370, 470, 570, 670 or 770. For example, when no insertion of the adhesive sheet 140, 240, 340, 440, 540 or 640 or incomplete attachment of the cover 120, 220 or 320 is detected by the magnetic sensor or the limit sensor, the display unit 281 may emit indication light, which may indicate a signal indicating incomplete preparation for operation. The side portion 411 may be provided in plural. For example, the side portion 411b is disposed on a side surface of the main body 410 corresponding to the side portion 411a inside the main body 410 to prevent the weight of the main body from being concentrated in a direction in which the side portion 411a is disposed, thereby further improving efficiency in trapping flies through stable installation of the insect trap.

The securing member 414 as shown in FIGS. 31 and 32 serves to secure the adhesive sheet 140 inserted into the main body 410 and may press an outer peripheral surface of the adhesive sheet 140. By way of example, the adhesive sheet 140 may include a sheet 142 and a flypaper piece 141 separated from the outer peripheral surface of the sheet 142 by a predetermined distance, and the securing member 414 may press the sheet 142 on which an adhesive liquid is not deposited or coated.

The securing member 414 may be a rotatable member to allow easy insertion and separation of the adhesive sheet 140. By way of example, the securing member 414 may be rotated such that a portion of the securing member 414 applying compressive force to the adhesive sheet 140 upon insertion of the adhesive sheet 140 into the main body 410 is placed outside a movement path of the adhesive sheet 140 so as not to obstruct movement of the adhesive sheet 140, and may be rotated back to press the sheet 142 after the adhesive sheet 140 is inserted into the main body 410. The securing member 414 will be described in detail with reference to FIG. 35 and FIG. 36.

That is, the adhesive-type insect trap includes the rotatable securing member 414 to allow easy insertion and separation of the adhesive sheet 140 while allowing stable installation of the adhesive sheet 140 within the main body, thereby improving user convenience and insect trapping efficiency of the adhesive sheet 140.

Figure 35:
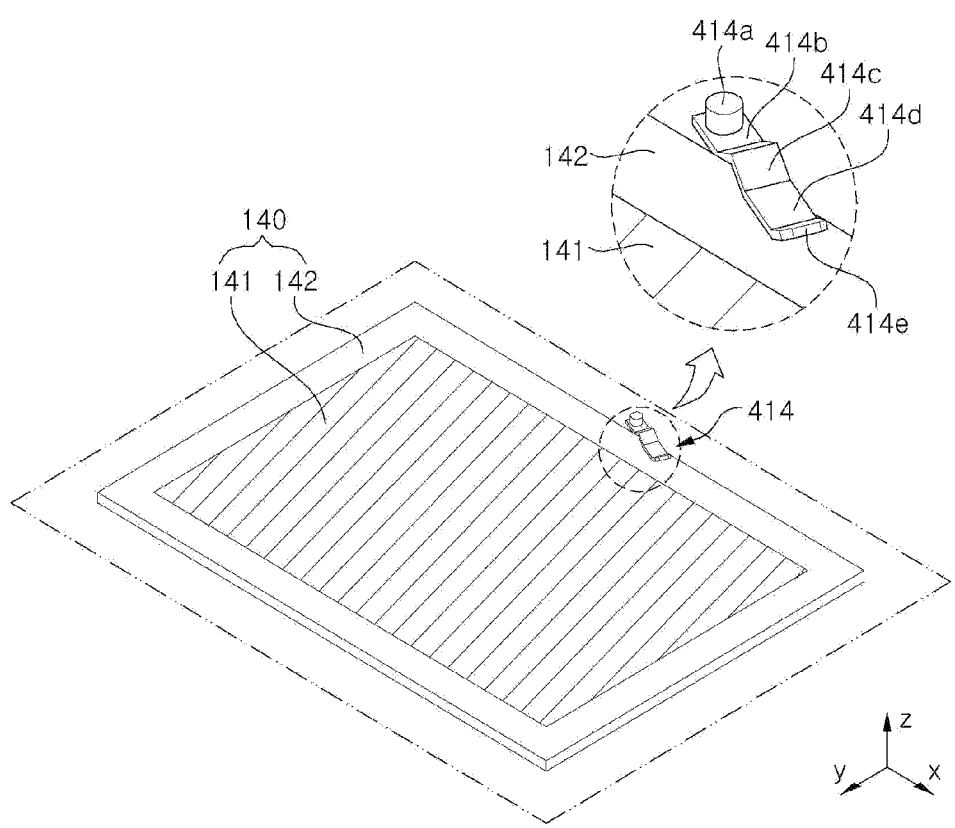
FIG. 35 shows an enlarged view of the adhesive sheet secured to the main body by a securing member according to embodiments of the present disclosure.
Figure 36A:
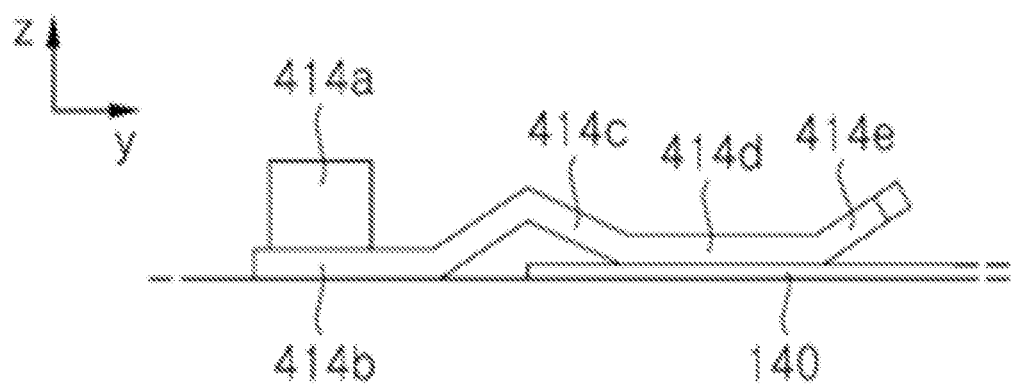
FIG. 36(a) shows a cross-section view of the adhesive sheet of FIG. 35
Figure 36B:
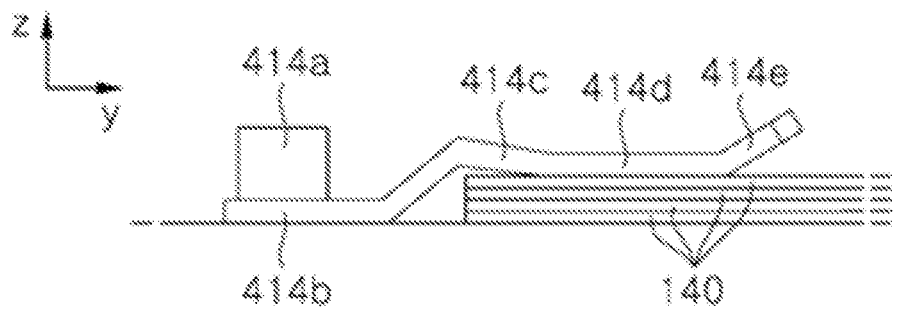
FIG. 36(b) shows another cross-section view of the adhesive sheet of FIG. 35.

FIG. 35 and FIG. 36 show an adhesive sheet secured by a securing member according to one embodiment of the present disclosure. Referring to FIG. 35 and FIG. 36, the securing member 414 may include a rotating portion 414a, a connecting portion 414b, a bent portion 414c, a pressing portion 414d, and a tongue portion 414e.

The rotating portion 414a is a portion imparting rotational force to the securing member 414 and may have any shape capable of imparting rotational force thereto. For example, the rotating portion 414a may be a hinge. The connecting portion 414b is connected to the rotating portion 414a and may be configured to restrict movement of the rotating portion 414a in a height direction in order to achieve efficient generation of resilient force described below. The bent portion 414c is a portion generating resilient force to allow the securing member 414 to press a single or plurality of adhesive sheets 140. The bent portion 414c is bent in a substantially ∧ shape or in a substantially V shape from the connecting portion 414b and extends therefrom to impart resilient force to the securing member 414, and may be further provided with various resiliency imparting members such as a resilient piece, a spring, a cylinder, and the like. The pressing portion 414d extends from the bent portion 414c to apply compressive force to the sheet 142 and may include a flat surface formed on at least a portion thereof. The tongue portion 414e is provided to allow a user to easily lift the pressing portion 414d in order to insert the adhesive sheet 140 into a space between the pressing portion 414d and the main body bottom 410a. The tongue portion 414e extends from the pressing portion 414d and may have a distal end separated a predetermined distance from the sheet.

Figure 37A:
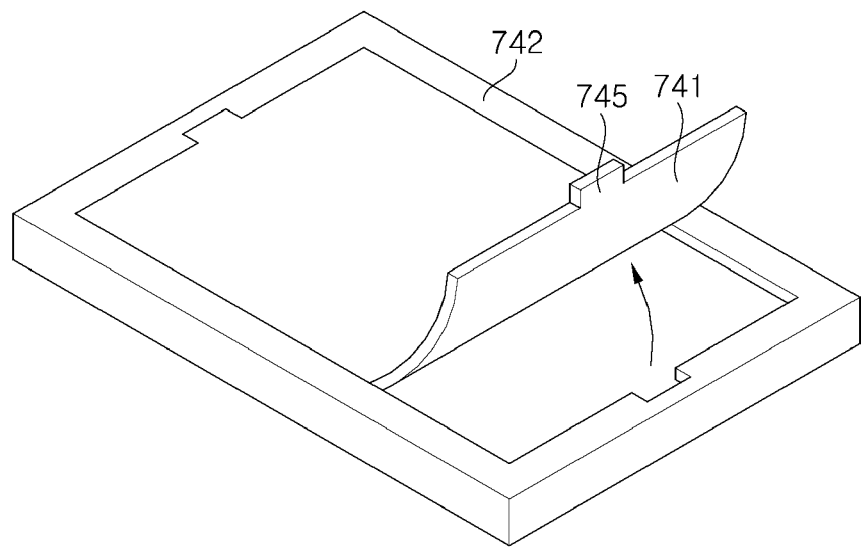
FIG. 37(a) shows an adhesive sheet according to one embodiment of the present disclosure.
Figure 37B:
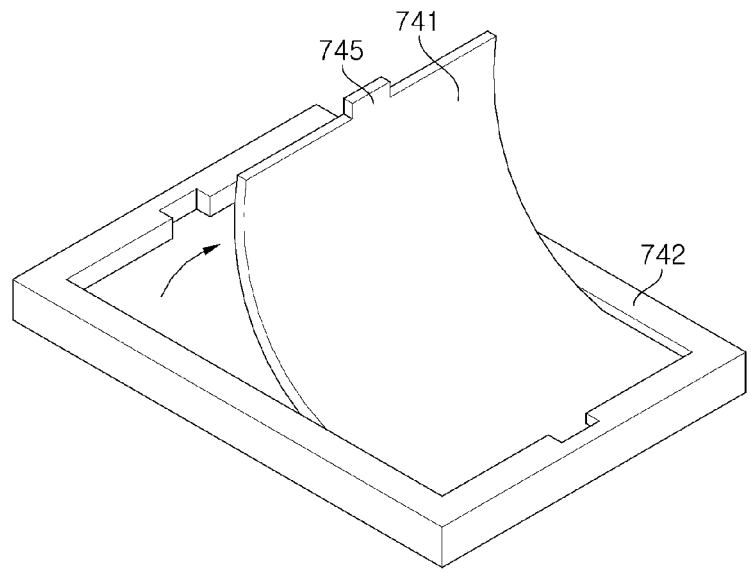
FIG. 37(b) shows the different view of FIG. 37(a).

For example, the securing member 414 may secure one adhesive sheet 140 by pressing the adhesive sheet 140, as shown in FIG. 36(a), or may secure a plurality of adhesive sheets 140 by pressing the adhesive sheets 140, as shown in FIG. 37(b). For example, the securing member 414 includes the bent portion 414c, which is bent in a substantially ∧ shape or in a substantially V shape from the connecting portion 414b and extends therefrom to impart resilient force to the securing member 414, whereby the pressing portion 414d can impart compressive force to sufficiently press the plurality of adhesive sheets 140.

That is, the securing member 414 is rotatable and is configured to generate resilient force to impart sufficient compressive force to the plurality of adhesive sheets 140, thereby improving user convenience and insect trapping efficiency of the adhesive sheet 140.

FIG. 37 shows an adhesive sheet according to one embodiment of the present disclosure. Referring to FIG. 37, an adhesive sheet 740 includes a sheet 742 and a plurality of flypaper pieces 741. The sheet 742 defines a space having a predetermined thickness to allow the plurality of flypaper pieces 741 to be stacked therein and has a rim formed along an outer peripheral surface of the space defined to receive the plurality of flypaper pieces 741 stacked therein. The rim refers to a portion to which compressive force is applied from the securing member 413 upon insertion of the adhesive sheet 740 into the main body 410 and has a predetermined area to allow a user to grip the rim upon insertion or separation of the adhesive sheet 740 into or from the main body 410.

The plural flypaper pieces 741 may allow a user to sequentially peel off the flypaper pieces 741 stacked one above another and may be stacked, for example, in a height direction of the adhesive sheet 740. For example, when one flypaper piece 741 disposed at an upper side is removed from another flypaper piece 741 disposed at a lower side, an adhesive surface of the other flypaper piece 741 may be exposed. In addition, each of the flypaper pieces 741 may further include a gripper 745. The gripper 745 may include a region coated with no adhesive liquid to allow a user to easily separate the flypaper piece 741 disposed at the upper side from the other flypaper piece 741 disposed at the lower side.

That is, the adhesive sheet 740 includes the plurality of flypaper pieces 741 stacked one above another to be conveniently peeled off, and thus can be stably secured within the main body 410, thereby improving insect trapping efficiency and durability of each component in the insect trap.

Figure 38:
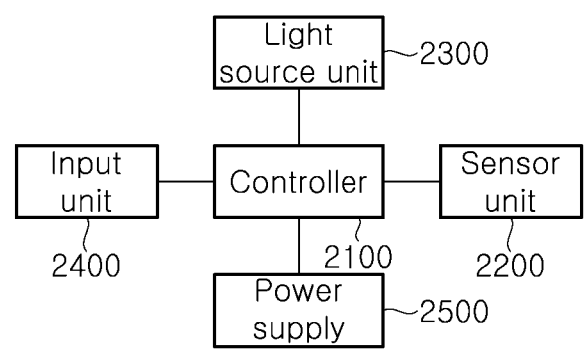
FIG. 38 is a block diagram of the adhesive-type insect trap according to the embodiments of the present disclosure.

FIG. 38 is a block diagram of the adhesive-type insect trap according to the embodiments of the present disclosure.

Referring to FIG. 38, the adhesive-type insect trap according to the embodiments of the present disclosure may include a controller 2100, a sensor unit 2200, a light source unit 2300, an input unit 2400, and a power supply 2500.

The controller 2100 may control operation of the adhesive-type insect trap, for example, operation of the light source unit 2300, based on input information. The controller 2100 may process at least part of information obtained from the sensor unit 2200 to provide the processed information to a user in various ways or to control operation of the light source unit 2300 based on the processed information.

The power supply 2500 supplies electric power to the adhesive-type insect trap and may be charged using a general AC power source or may include a battery. The power supply 2500 may include a filter, a rectifier, a switching converter, and an output unit. The filter prevents internal components of the power supply 2500 from being damaged by noise on an input line and removes high-frequency noise over the audio band, thereby allowing stable current supply. The rectifier may be composed of a rectifying circuit, a smoothing circuit, and a constant voltage circuit. The rectifying circuit filters only the positive polarity from an alternating current that oscillates at 50 Hz to 60 Hz per second, the smoothing circuit converts a pulsed current into a constant voltage using a rectifier capacitor keeping a voltage constant, and the constant voltage circuit may be composed of a constant voltage diode producing a stable and constant direct current and a transistor. The switching converter may reduce electric power converted into a constant current by the rectifier into DC power required by a phototherapy apparatus. The output unit may supply power to the light source unit 2300.

The light source unit 2300 may be operated in response to an operation signal from the controller 2100. For example, based on information detected by the sensor unit 2200, the controller 2100 may control power supply to the light source unit 2300 or control operation of the light source 170, 270, 370, 470, 570, 670 or 770.

By way of example, the controller 2100 may control operation of the light source 170, 270, 370, 470, 570, 670 or 770 based on information detected by a first sensor 760 or a second sensor 780 (FIGS. 41-42) that detects whether the adhesive sheet 140, 240, 340, 440, 540, 640 or 740 is inserted and whether the cover 120, 220 or 320 is attached. For example, when the adhesive sheet 170, 270, 370, 470, 570, 670 or 770 is incompletely inserted or the cover 120, 220, or 320 is incompletely attached to the main body 110, 210 or 310, the controller 2100 may send a signal for cutting off power supply to the light source 170, 270, 370, 470, 570, 670 or 770 to the light source unit 2300 after receiving corresponding information detected by the first sensor 760 or the second sensor 780. That is, when the adhesive sheet 140, 240, 340, 440, 540, 640 or 740 is incompletely inserted or the cover 120, 220 or 320 is incompletely attached, the adhesive-type insect trap shuts off operation of the light source 170, 270, 370, 470, 570, 670 or 770 to inform a user of incomplete insertion of the adhesive sheet or incomplete attachment of the cover, thereby improving insect trapping efficiency.

The input unit 2400 may be provided in the form of a keyboard including various keys such as character buttons, symbol buttons, special buttons and the like to receive user input or may be provided in the form of a simple switch. Although not shown in the drawings, for the adhesive-type insect trap further including a display unit (not shown), the display unit may be implemented as, for example, a touchscreen panel. Here, the keyboard included in the input unit 2400 may be displayed to overlap a touchscreen in graphical form. Here, the location and transparency of a keyboard input window are adjustable by a user and the touchscreen panel may include an input means that serves as a display means and registers input by detecting the touch of a finger or stylus on a surface thereof.

Although not shown in the drawings, the adhesive-type insect trap may further include the display unit (not shown). The display unit may display a window, for example, a graphical user interface (GUI), displaying information on operation of each component of the adhesive-type insect trap, operation of which is controlled by the controller 2100, for example, information on operation of the light source 170, 270, 370, 470, 570, 670 or 770 or information detected by the sensor unit 2200, and may be disposed, for example, on a front surface of the cover 120, 220 or 320. The display unit may be implemented as a display window such as an LCD or an LED, or may be implemented as a touchscreen panel serving as both an input means and a display means. By way of example, when information such as incomplete insertion of the adhesive sheet 140, 240, 340, 440, 540, 640 or 740 is detected by the first sensor 760 or the second sensor 780, the information may be sent to a user through the display unit. By way of example, information on insects, for example, an amount of trapped insects, the kind of insect, a danger level of insects, and the like, detected by an insect information detection sensor 790 may be displayed on the display unit.

Although not shown in the drawings, the adhesive-type insect trap may further include an alarm generator (not shown). When a data value detected by the sensor unit 2200 exceeds or is less than a preset data value, the controller 2100 may send an alarm generation signal to the alarm generator. Here, an alarm generated by the alarm generator may be a sound alarm or a light alarm and may be issued from an electronic device of a user, for example, a portable terminal, through a communication module. For example, when the first sensor 760 or the second sensor 780 detects that the adhesive sheet 140, 240, 340, 440, 540, 640 or 740 is not inserted into the main body or that the cover 120, 220 or 320 is incompletely attached to the main body, the alarm generator may generate an alarm which may serve as a not-ready signal. For example, when the amount of trapped insects detected by the insect information detection sensor 790 exceeds a preset value, the alarm generator may generate an alarm which may serve as a signal for replacement of the adhesive sheet 140, 240, 340, 440, 540, 640 or 740.

Figure 39:
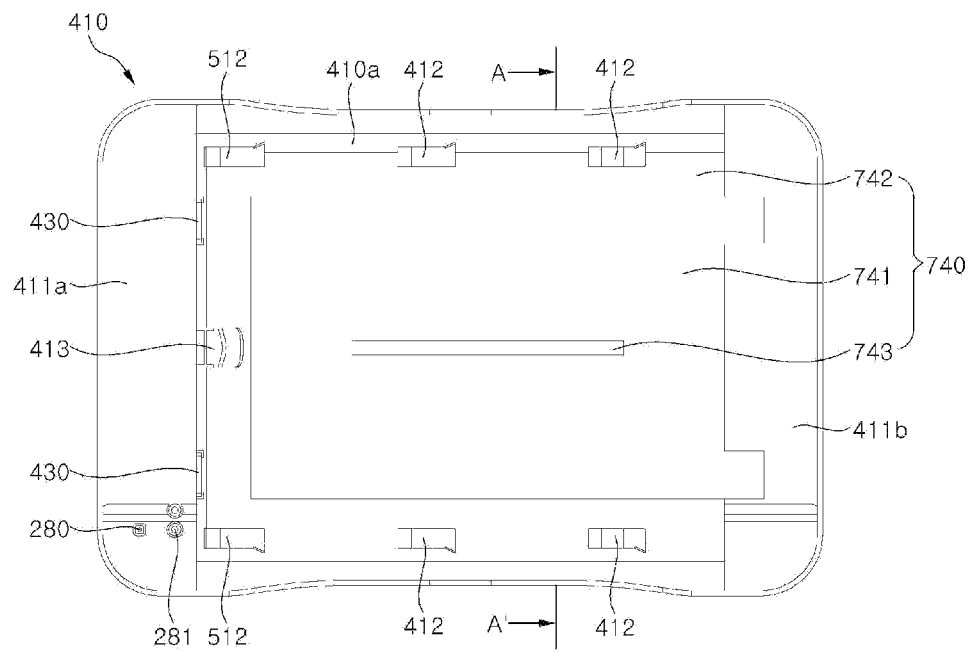
FIG. 39 shows a main body separated from an adhesive-type insect trap according to the embodiments of the present disclosure.
Figure 40:
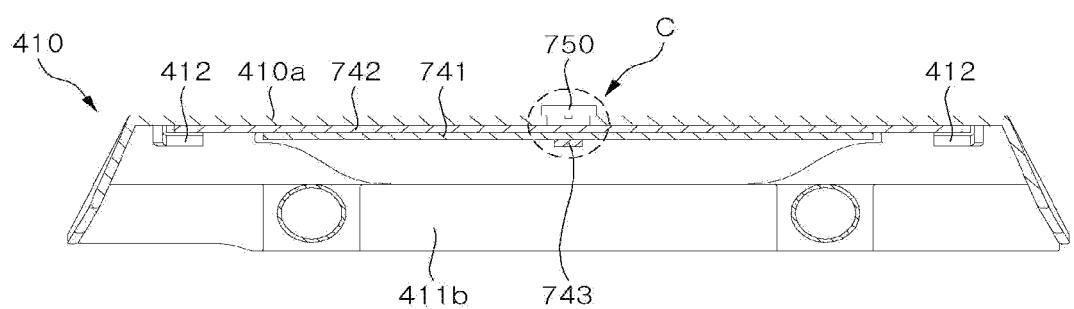
FIG. 40 is a cross-sectional view taken along line A-A' of FIG. 39.
Figure 41A:
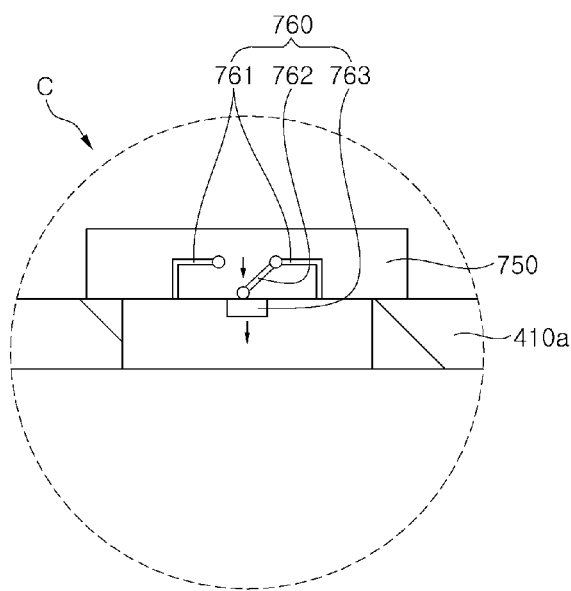
FIG. 41(a) is an enlarged view of Region C of FIG. 40 with no power supply to a light source and FIG. 41(b) shows the photosensor allowing the power supply to a light source.
Figure 41B:
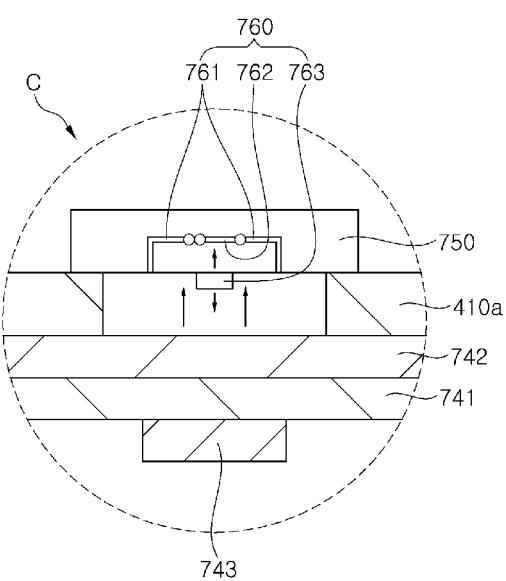

FIG. 39 shows the adhesive-type insect trap according to the embodiment of the present disclosure, from which a main body is separated, FIG. 40 is a cross-sectional view taken along line A-A' of FIG. 39, and FIG. 41 is an enlarged view of Region C of FIG. 40.

Referring to FIG. 39, the main body 410 of the adhesive-type insect trap includes a main body bottom 410a, side portions 411a, 411b, an adhesive sheet 740, a guide member 412, a stopper unit 413, and securing members 743, 750.

The main body bottom 410a refers to a region in which the adhesive sheet 740 is inserted into the main body and disposed at an upper side thereof, the side portions 411a, 411b are disposed at both sides thereof, and the guide member 412 and the stopper unit 413 are disposed. The side portions 411a, 411b may adjoin the side surfaces of the main body 410 or may be separated a predetermined distance from the main body 410. For example, the side portions may be disposed to adjoin the side surfaces of the main body 410 to allow efficient use of a space defined in the main body 410. The side portions 411a, 411b may be provided with the light source mount 430, circuits (not shown), and a power supply (not shown), which supplies power to the light source 170, 270, 370, 470, 570, 670 or 770, the sensor 280, the display unit 281, and the like, and may include a separate housing to prevent damage to the power supply and the circuit due to intrusion of insects or dust. The side portion 411 may be provided in plural. For example, the side portion 411b is disposed on a side surface of the main body 410 corresponding to the side portion 411a inside the main body 410 to prevent the weight of the main body from being concentrated in a direction in which the side portion 411a is disposed, thereby further improving efficiency in trapping flies through stable installation of the insect trap.

The guide member 412 guides the adhesive sheets 740 to be stably inserted into the main body 410 and may be provided in plural. For example, the guide members 412 may be separated from each other by a predetermined distance. By way of example, at least two guide members 412 may be disposed on opposite surfaces with reference to the adhesive sheet 140, 240, 340, 440, 540 or 640. For example, three guide members 412 may be disposed on each of the opposite surfaces with reference to the adhesive sheet 740. Here, the guide members 412 disposed at locations at which the adhesive sheet 740 reaches the deepest depth may include a wall having a predetermined height to stop movement of the adhesive sheet 740. That is, the adhesive-type insect trap allows the adhesive sheet 740 to be inserted along the plural guide members 412 separated from each other by a predetermined distance, instead of being inserted along the guide rails extending in an insertion direction of the adhesive sheet 740, thereby preventing difficulty in insertion and separation of the adhesive sheet 740 due to attachment of the adhesive sheet 740 to the guide rails, or further improving efficiency in trapping flies by securing a larger area for trapping flies.

Figure 42A:
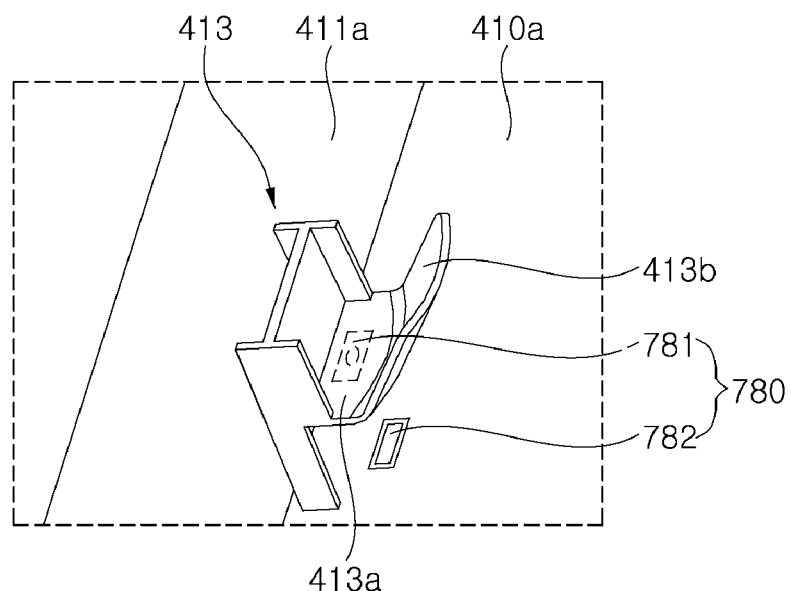
FIG. 42(a) shows one signal reception state of a light reception sensor according to one embodiment of the present disclosure.
Figure 42B:
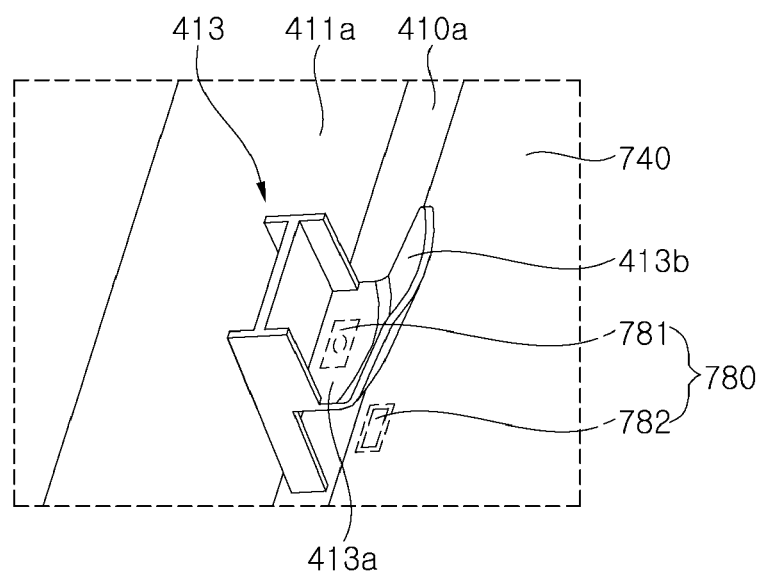
FIG. 42(b) shows another signal reception state of the light reception sensor.

The stopper unit 413 allows the adhesive sheet 740 to be stably inserted into the main body 410 and secured thereto, and may be provided singularly or in plural. For example, the stopper unit 413 may be disposed between the plural light source mounts 430. As shown in FIG. 42, the stopper unit 413 includes a stopper plate 413a and a tongue portion 413b. The stopper plate 413a may be substantially perpendicular to the main body bottom 410a and allows the adhesive sheet 740 to be inserted into and secured in a space defined between the stopper plate 413a and the main body bottom 410a. The tongue portion 413b is slanted in a direction in which the adhesive sheet insertion hole 113 is disposed, and serves to allow a distal end of the adhesive sheet 740 to be smoothly inserted into the space between the stopper plate 413a and the main body bottom 410a along the tongue portion 413b. For example, the tongue portion 413b has a round shape, for example, a substantially U shape, which convexly protrudes towards the adhesive sheet insertion hole 113, and serves to guide the distal end of the adhesive sheet 740 to be smoothly inserted into the space between the stopper plate 413a and the main body bottom 410a along the tongue portion 413b when inserted into the main body 410. When the stopper plate 413a is composed of a resilient piece, the stopper plate 413a may be disposed to adjoin the main body bottom 410a. For example, a user may secure the adhesive sheet 740 to the stopper unit 413 by applying force to the tongue portion 413b in an insertion direction of the adhesive sheet 740 to form a space between the stopper plate 413a and the main body bottom 410a, and inserting the adhesive sheet 740 into the space, followed by releasing the force applied to the tongue portion 413b. As such, the adhesive-type insect trap includes the stopper unit 413 to secure the adhesive sheet 740 to the stopper unit 413, in which the tongue portion 413b of the stopper unit 413 is slanted in a predetermined direction to allow the adhesive sheet 740 to be smoothly inserted into and secured to the main body without being bent, whereby the adhesive sheet 740 adapted to directly trap flies and the like can be stably secured in the insect trap, thereby improving efficiency in trapping flies and the like.

The securing members 743, 750 serve to prevent the adhesive sheet 740 from being bent due to the weight of the adhesive sheet or heat generated from the light source. The securing members 743, 750 include a first securing member 743 disposed on at least a portion of the adhesive sheet 740 to be inserted into the main body and a second securing member 750 disposed to face the first securing member 743. The locations of the first securing member 743 and the second securing member 750 are not particularly limited. For example, the first securing member 743 and the second securing member 750 may be disposed substantially at the center of the adhesive sheet 740 to improve efficiency in securing the adhesive sheet 740 even with a minimum area. Although the adhesive sheet 740 may be secured in any shape without being limited to a particular shape, for example, at least part of the adhesive sheet 740 may be brought into tight contact with the main body bottom 410a by compressive force generated due to interaction between the first securing member 743 and the second securing member 750. Here, although the first securing member 743 may be disposed at any location, for example, on an upper surface of the flypaper piece 741, between the flypaper piece 741 and the sheet 742, or on a lower surface of the sheet 742, it is desirable that the first securing member 743 be disposed on the upper surface of the flypaper piece 741 in order to securely prevent bending of the flypaper piece 741. Further, the second securing member 750 may be disposed on the main body bottom 410a or on a back surface of the main body bottom 410a. In order to secure a space for receiving the first sensor 760 and to allow efficient use of an inner space of the main body 410, the second securing member 750 may be disposed on the back surface of the main body bottom 410a. On the other hand, compressive force generated by the first securing member 743 and the second securing member 750 may include magnetic force and at least one of the first securing member 743 and the second securing member 750 may generate magnetic force.

Not only do the securing members 743, 750 prevent the adhesive sheet 740 from being bent, but also may detect incomplete insertion or no insertion of the adhesive sheet 740. By way of example, referring to FIG. 41, the second securing member 750 may include a first sensor 760. Here, the first sensor 760 may control power supply to the light source 770 through the controller 2100 so as not to supply power to the light source 770 mounted on the light source mount 430 when the adhesive sheet 740 is not inserted into the main body 410 to reach a particular location therein. For example, the first sensor 760 may be implemented by various sensors capable of generating a ground signal. When various components are connected to or disconnected from, for example, a chassis ground, the ground signal may be generated to detect whether the adhesive sheet 740 is inserted into the main body 410 to reach a particular location. For example, the first sensor 760 includes a magnetic sensor that detects grounding of the components based on magnetic force. The first sensor 760 prevents the adhesive sheet 740 from being bent during use of the adhesive sheet 740 brought into tight contact with the main body bottom 410a, and controls the power supply so as not to supply power to the light source 770 mounted on the light source mount 430 when the adhesive sheet 740 is not inserted into the main body 410 to reach a particular location therein, thereby improving insect trapping efficiency through efficient use of the interior space of the main body 410. The first sensor 760 may be implemented by various sensors as well as the magnetic sensor for generating the ground signal. For example, the first sensor 760 may be implemented by a photosensor, such as a photo interrupter sensor, a photoreflector sensor, and an IR sensor, to prevent obstruction of an insect trapping path by minimizing a space of the main body 410 occupied by the first sensor 760, thereby improving insect trapping efficiency. Further, the first sensor 760 may be implemented by a micro-switch to allow waterproofing and moisture proofing while preventing damage by secreted materials of insects trapped in the insect trap.

For example, referring to FIGS. 41(*a*) and 41(*b*), the magnetic sensor 760 may include a connection pin 761, a ground pin 762, and a magnet 763. FIG. 41(*a*) shows the adhesive sheet 740 not inserted into the main body 410, in which the ground pin 762 is not grounded to the connection pin 761 due to magnetic force generated by the magnet 763, whereby power is not supplied to the light source 770. FIG. 41(*b*) shows the adhesive sheet 740 inserted into the main body 410, in which the first securing member 743 disposed on the adhesive sheet 740 generates magnetic force towards the ground pin 762. Here, the magnetic force generated from the first securing member 743 has an opposite polarity to and is stronger than magnetic force generated from the magnet 763 such that the ground pin 762 is connected to the connection pin 761, thereby allowing power supply to the light source 770.

That is, the adhesive-type insect trap according to the embodiment can prevent unnecessary power consumption by preventing operation of the light source 770 when the adhesive sheet 740 is not inserted into the main body 410, and can improve insect trapping efficiency by preventing operation of the light source when the adhesive sheet 740 is incompletely inserted into the main body 410.

FIGS. 42(*a*) and (*b*) show a photosensor according to one embodiment of the present disclosure. The second sensor 780 may detect whether the adhesive sheet 740 is inserted into the main body or whether the adhesive sheet is stably inserted into the main body, and may control the light source 770 not to operate when it is detected that the adhesive sheet 740 is not inserted into the main body 410 or is incompletely inserted into the main body 410. The second sensor 780 may include, for example, a photosensor. The second sensor 780 may include a light reception sensor 782 and a light emission sensor 781. One of the light reception sensor 782 and the light emission sensor 781 may be disposed on the main body bottom 410a, and the other of the light emission sensor 781 and the light reception sensor 782 may be disposed on the side portion 411, 411a or 411b, the cover 120, 220 or 320, the light source mount 430, the stopper unit 413, and the like. For example, the second sensor 780 may be provided to the stopper unit 413, for example, on the stopper plate 413a, as shown in FIG. 42. Here, when the adhesive sheet 740 is not inserted into the main body 410 or is incompletely inserted into the main body 410, as shown in FIG. 42(*a*), a photo signal sent from the light emission sensor 781 to the light reception sensor 782 may be maintained and the controller 2100 may cut-off power supply to the light source 770. In addition, when the adhesive sheet 740 is inserted into the main body 410 to reach a particular location or more, as shown in FIG. 42(*b*), the photo signal sent from the light emission sensor 781 to the light reception sensor 782 may be blocked and the controller 2100 may control the light source 770 to be in an operable state.

That is, the second sensor 780 according to the embodiment of the present disclosure serves to control the power supply not to supply power to the light source 770 when the adhesive sheet 740 is not inserted into the main body 410 to reach a particular location therein. As such, the second sensor 780 is provided to the stopper unit 413 disposed where the adhesive sheet 740 is inserted into the main body 410 to be disposed at the deepest location therein or to be most stably disposed therein, thereby enabling efficient detection of whether the adhesive sheet 740 is stably inserted into the main body.

On the other hand, the second sensor may be implemented by at least one of various sensors applicable to the first sensor described above.

Figure 43:
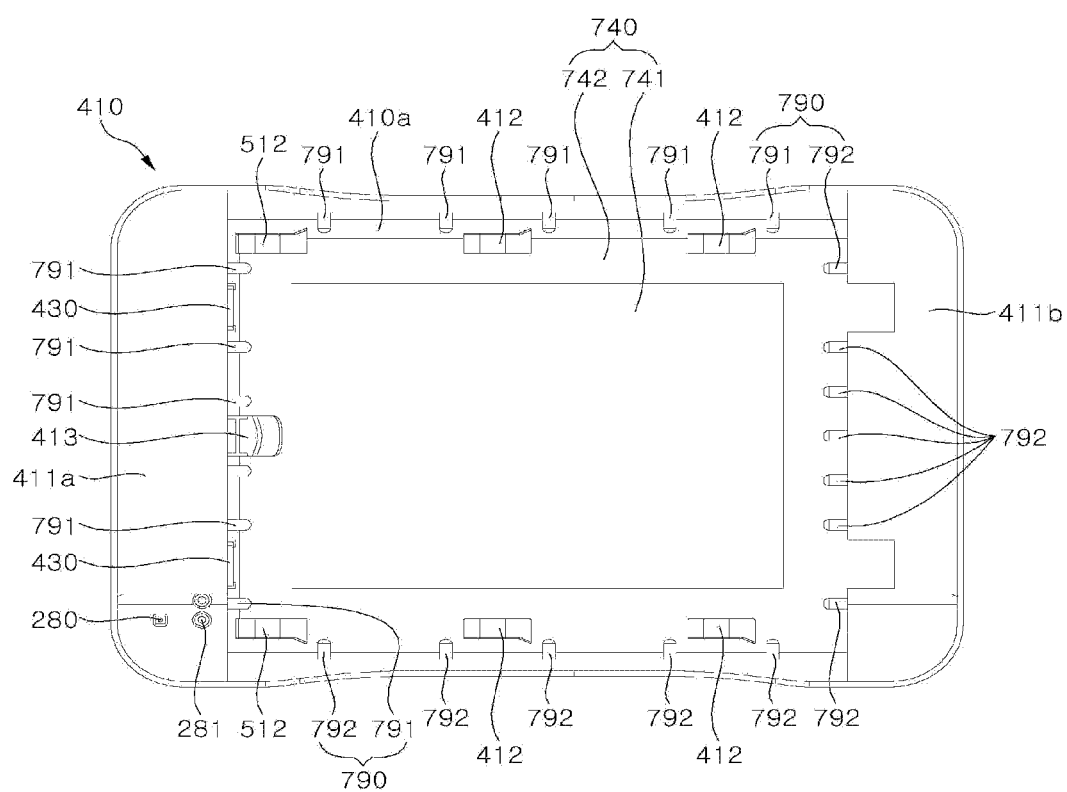
FIG. 43 shows an adhesive-type insect trap according to one embodiment of the present disclosure, with a cover separated therefrom.
Figure 44:
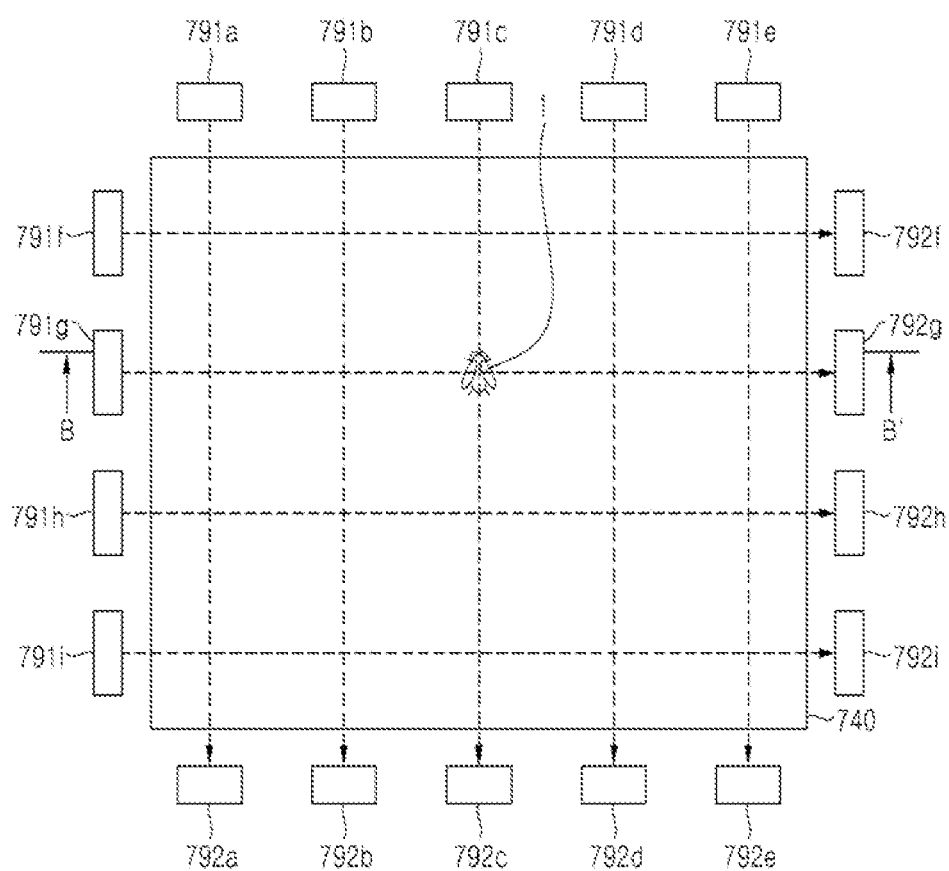
FIG. 44 is a conceptual diagram of operation of an insect information detection sensor shown in FIG. 43.
Figure 45:
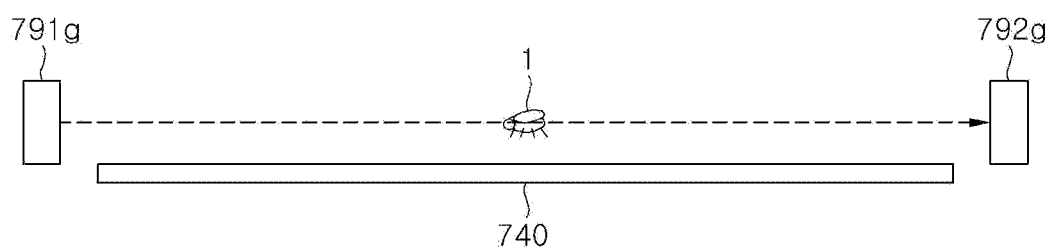
FIG. 45 shows cross-sectional views taken along line B-B' of FIG. 44.
Figure 46:
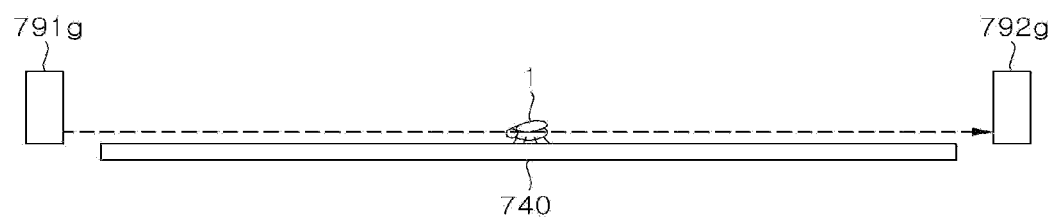
FIG. 46 are cross-sectional views taken along line B-B' of FIG. 44.

FIG. 43 shows an adhesive-type insect trap according to one embodiment of the present disclosure, with a cover separated therefrom, FIG. 44 is a conceptual diagram of operation of an insect information detection sensor shown in FIG. 43, and FIG. 45 and FIG. 46 are cross-sectional views taken along line B-B' of FIG. 44.

Referring to FIG. 43, the adhesive-type insect trap may further include an insect information detection sensor 790. The insect information detection sensor 790 may detect information on insects having entered the main body 410 or information on insects trapped on the adhesive sheet 740, in which the information on insects includes information on the amount of trapped insects, the kind of insect, or a danger level of insects, and the like. By way of example, when the amount of trapped insects detected by the insect information detection sensor 790 exceeds a preset value, the controller 2100 may stop operation of the light source 770, the display unit may display a time for replacement of the adhesive sheet 740, or the alarm generator may generate an alarm.

By way of example, as shown in FIG. 43, the signal transmission unit 791 and the signal reception unit 792 may be disposed along the outer peripheral surface of the adhesive sheet 740 inserted into the main body 410, thereby enabling efficient detection of information on the amount of trapped insects over the entire area of the adhesive sheet 740. Here, the signal transmission unit 791 is disposed to face the signal reception unit 792 to receive light or sound waves generated from the signal transmission unit 791, and each of the signal transmission unit 791 and the signal reception unit 792 may be provided in plural.

For example, the insect information detection sensor 790 may employ light, for example, IR light. When the signal reception unit 792 does not receive light emitted from the signal transmission unit 791 due to insects blocking the light, the insect information detection sensor 790 may detect information on passage of insects or trapping of insects and may be operated in a way that information on the amount of trapped insects is detected and calculated by the controller 2100 based on the number of passage or trapping times of insects or the number of signal reception units 792 not receiving a photo signal. For example, as shown in FIG. 44, the signal transmission unit 791 may include a first signal transmission unit 791*a*, a second signal transmission unit 791*b*, ..., and an n$^{th}$ signal transmission unit 791*n*, and the signal reception unit 792 includes a first signal reception unit 792*a*, a second signal reception unit 792*b*, ..., an n$^{th}$ signal reception unit 792*n* corresponding to the first to n$^{th}$ signal transmission units, respectively, to allow detection of information on insects passing through or trapped in spaces between the first signal transmission unit 791*a* and the first signal reception unit 792*a*, between the second signal transmission unit 791*b* and the second signal reception unit 792*b*, ..., and between the n$^{th}$ signal transmission unit 791*n* and the n$^{th}$ signal reception unit 792*n*. For example, as shown in FIG. 44, when at least one signal reception unit 792*g* or 792*c* does not receive a photo signal, information on trapping of an insect 1 may be detected. Here, as shown in FIG. 45, when an insect passes a particular location instead of being trapped on the adhesive sheet 740, the insect information detection sensor 790 may be operated, and, as shown in FIG. 46, when an insect 1 is trapped on the adhesive sheet 740, the insect information detection sensor 790 may be operated, and such configuration may be conveniently controlled through user manipulation.

That is, the adhesive-type insect trap according to the embodiment of the present disclosure further includes the insect information detection sensor 790 to determine a time for replacement of the adhesive sheet 740 based on the information on the amount of trapped insects, thereby preventing deterioration in insect trapping efficiency.

In accordance with one aspect of the present disclosure, an adhesive-type insect trap includes: a main body having an adhesive sheet insertion hole; a light source mount disposed on the main body; and a cover detachably attached to the main body and having a through-hole formed in at least a portion thereof. The adhesive sheet includes a flypaper piece and a sheet, and the main body includes a guide unit guiding the adhesive sheet and an adhesive sheet support supporting the adhesive sheet. An adhesive-type insect trap according to embodiments of the present disclosure can prevent the interior of the insect trap, particularly, insects collected therein, from being visibly observed from the outside while securing high insect trapping efficiency.

In addition, the adhesive-type insect trap according to the embodiments of the present disclosure may include an adhesive sheet secured to a main body thereof, thereby preventing the adhesive sheet having insects collected thereon from being easily separated from the main body.

Further, the adhesive-type insect trap according to the embodiments of the present disclosure allows light emitted from a light source thereof to be refracted or spread, thereby improving insect attraction efficiency with decoy light. Further, the adhesive-type insect trap according to the embodiments of the present disclosure may emit UV light to attract insects and may generate carbon dioxide, thereby further improving an insect attraction effect. Further, the adhesive-type insect trap according to the embodiments of the present disclosure has a deodorization effect, thereby providing a pleasant environment around the adhesive-type insect trap.

Further, the adhesive-type insect trap according to the embodiments of the present disclosure may include a UVC light source, thereby enabling killing of insects or sterilization of bacteria in insects trapped on the adhesive sheet within the insect trap. Further, the adhesive-type insect trap according to the embodiments of the present disclosure may include a camera or a sensor to allow a user to monitor the kind of insect trapped on the adhesive sheet or to determine a time for replacement of the adhesive sheet, may have an alarm function to inform a user of the time for replacement of the adhesive sheet, thereby improving user convenience, and may automatically or manually control the intensity of light emitted from a light source depending upon the quantity of light around the adhesive-type insect trap, thereby enabling economically feasible power consumption and extension of lifespan of the light source while improving insect attraction efficiency with decoy light. Further, the adhesive-type insect trap according to the embodiments of the present disclosure may include an insect attractant spray or an adhesive sheet containing an insect attractant, thereby improving insect attraction efficiency.

Although some embodiments have been described herein, it should be understood that these embodiments are provided for illustration only and are not to be construed in any way as limiting the present disclosure, and that the scope of the present disclosure should be defined by the appended claims and equivalents thereof.

The invention claimed is:

1. An adhesive-type insect trap comprising:
   a main body having an adhesive sheet insertion hole;
   a light source mount disposed on the main body; and
   a cover detachably attached to the main body and having a through-hole formed in at least a portion thereof,
   an adhesive sheet comprising a flypaper piece and a sheet,
   wherein the main body comprises:
   a guide unit including at least two groups of a plurality of guide members including a first group and a second group,
   the first group disposed on a first side of a main body bottom and the second group disposed on a second side of the main body bottom opposing the first side such that the adhesive sheet is placed on the main body bottom between the first group and the second group and secured by the first group and the second group on the first side and the second side, and
   a guide member of the plurality of guide members comprising at least two plates having different heights from the main body bottom; and
   a stopper unit disposed on a third side of the main body bottom, perpendicular to the first and the second side, and configured to stop movement of the adhesive sheet guided into the main body, and
   wherein the cover comprises a cover protrusion configured to prevent the adhesive sheet from contacting a light source and disposed on a surface of a through-hole blocking structure configured to block at least a portion of the through-hole, the surface of the through-hole blocking structure being concavely depressed towards an interior of the cover, and wherein the cover protrusion has a height extending from the surface of the through-hole blocking structure to the main body and has a cross-sectional area gradually decreasing from the surface of the through-hole blocking structure to the main body.

2. The adhesive-type insect trap according to claim 1, further comprising a sensor operable to detect:
at least one of kind of insects trapped on the adhesive sheet,
an area of the adhesive sheet trapping insects,
brightness of the adhesive sheet, an ambient temperature of the light source,
intensity of light emitted from the light source,
ambient illuminance of the insect trap,
insertion of the adhesive sheet into the insect trap,
attachment of the cover to the main body, or a combination thereof.

3. The adhesive-type insect trap according to claim 1, wherein the at least two plates of the guide member comprises a first plate arranged adjacent to the adhesive sheet insertion hole and the first plate has a greatest height relative to the main body bottom.

4. The adhesive-type insect trap according to claim 3, wherein the at least two plates of the guide member comprises:
a second plate having a lowest height relative to the main body bottom; and
a slanted portion disposed between the first and the second plates,
the slanted portion having an inclination having an angle formed relative to the main body bottom.

5. The adhesive-type insect trap according to claim 4, wherein the guide member further comprises an end wall disposed in a width direction of the second plate to stop movement of the adhesive sheet and extending from the main body bottom.

6. The adhesive-type insect trap according to claim 1, wherein the stopper unit comprises a stopper plate and a tongue portion, the tongue portion being slanted in a direction in which the adhesive sheet insertion hole is disposed.

7. The adhesive-type insect trap according to claim 6, wherein the tongue portion comprises a convexly round shape in the direction in which the adhesive sheet insertion hole is disposed.

8. The adhesive-type insect trap according to claim 7, wherein the adhesive sheet is guided to a space between the stopper plate and the main body bottom along a slanted surface of the tongue portion slanted in the direction in which the adhesive sheet insertion hole is disposed.

9. The adhesive-type insect trap according to claim 1, wherein a region of the cover protrusion having a smallest cross-sectional area is disposed at a distal end of the cover protrusion closer toward the main body bottom than the cover.

10. The adhesive-type insect trap according to claim 1, further comprising: a sensor comprising a light reception sensor and a light emission sensor to prevent electric power from being supplied to the light source mounted on the light source mount when the adhesive sheet is not inserted into the main body to reach a predetermined location therein,
wherein the stopper unit extends from the main body bottom,
at least one of the light reception sensor and the light emission sensor is disposed on the main body bottom, and
the light emission sensor disposed on the main body bottom to face the light reception sensor or the light reception sensor disposed on the main body bottom to face the light emission sensor is provided to the stopper unit.

11. The adhesive-type insect trap according to claim 10, wherein the stopper unit comprises a stopper plate and a tongue portion slanted in a direction in which the adhesive sheet insertion hole is disposed, and the light emission sensor disposed on the main body bottom to face the light reception sensor or the light reception sensor disposed on the main body bottom to face the light emission sensor is provided to the stopper plate.

12. The adhesive-type insect trap according to claim 1, wherein the main body comprises a signal transmission unit and a signal reception unit disposed along an outer periphery of the adhesive sheet inserted into the main body,
the signal transmission unit sending a signal,
the signal reception unit receiving the signal sent from the signal transmission unit; and
wherein the signal transmission unit and the signal reception unit are disposed to face each other and the signal reception unit receives the signal sent from the signal transmission unit.

13. The adhesive-type insect trap according to claim 12, wherein the signal transmission unit comprises three or more signal transmission units including a first signal transmission unit, a second signal transmission unit, and an $n^{th}$ signal transmission unit, and
the signal reception unit comprises three or more signal reception units comprising a first signal reception unit, a second signal reception unit, and an $n^{th}$ signal reception unit corresponding to the first signal reception unit to the $n^{th}$ signal transmission unit, respectively,
wherein the signal transmission units and the signal reception units operate to detect information on insects passing through or trapped in spaces between the first signal transmission unit and the first signal reception unit, between the second signal transmission unit and the second signal reception unit, and between the $n^{th}$ signal transmission unit and the $n^{th}$ signal reception unit.

14. The adhesive-type insect trap according to claim 13, wherein the information on insects comprises a number of insects trapped therein.

15. An adhesive-type insect trap comprising:
a main body having an adhesive sheet insertion hole;
a light source mount disposed on the main body; and
a cover detachably attached to the main body and having a through-hole formed in at least a portion thereof,
an adhesive sheet comprising a flypaper piece and a sheet; and
a sensor for detecting intensity of light emitted from a light source;
a guide unit guiding the adhesive sheet and including two or more groups of a plurality of guide members and a stopper unit:
the two or more groups of a plurality of guide members including a first group and a second group and the first group and the second group being disposed on a surface of the main body on which the adhesive sheet is placed and at opposing sides of the surface of the main body such that the adhesive sheet is placed on the surface of a main body bottom between the first group and the second group and secured by the first group and the second group on the opposing sides, and wherein a guide member of the plurality of guide members includes at least two plates having different heights from the main body bottom; and wherein the stopper unit is disposed on a side perpendicular to the opposing sides of the surface of the main body and configured to stop movement of the adhesive sheet guided into the main body, and wherein the cover comprises a cover protrusion configured to prevent the adhesive sheet from contacting the light source and disposed on a surface of a through-hole blocking structure configured to block at least a portion of the through-hole, the surface of the through-hole blocking structure being concavely depressed towards an interior of the cover, and wherein the cover protrusion has a height extending from the surface of the through-hole blocking structure to the main body and has a cross-sectional area gradually decreasing from the surface of the through-hole blocking structure to the main body.

* * * * *